(12) United States Patent
Vogelbacher et al.

(10) Patent No.: US 10,093,634 B2
(45) Date of Patent: Oct. 9, 2018

(54) PROCESS FOR THE PREPARATION OF SUBSTITUTED PHENOXYPHENYL KETONES

(71) Applicant: BASF Agro B.V., Arnhem (NE)

(72) Inventors: Uwe Josef Vogelbacher, Ludwigshafen (DE); Joachim Gebhardt, Ludwigshafen (DE); Michael Rack, Eppelheim (DE); Roland Goetz, Neulussheim (DE); Stefan Fuelster, Worms (DE)

(73) Assignee: BASF AGRO B.V., Arnheim (NL)

( * ) Notice: Subject to any disclaimer, the term of this patent is extended or adjusted under 35 U.S.C. 154(b) by 0 days.

(21) Appl. No.: 15/105,232

(22) PCT Filed: Dec. 8, 2014

(86) PCT No.: PCT/EP2014/076839
§ 371 (c)(1),
(2) Date: Jun. 16, 2016

(87) PCT Pub. No.: WO2015/091045
PCT Pub. Date: Jun. 25, 2015

(65) Prior Publication Data
US 2016/0318881 A1    Nov. 3, 2016

(30) Foreign Application Priority Data

Dec. 18, 2013  (EP) ..................................... 13197924
Oct. 2, 2014   (EP) ..................................... 14187515

(51) Int. Cl.
| C07C 45/00 | (2006.01) |
| C07C 45/64 | (2006.01) |
| C07C 49/80 | (2006.01) |
| C07C 249/08 | (2006.01) |
| C07C 25/13 | (2006.01) |
| C07D 249/08 | (2006.01) |
| C07F 3/02 | (2006.01) |

(52) U.S. Cl.
CPC ............ *C07D 249/08* (2013.01); *C07C 25/13* (2013.01); *C07C 45/004* (2013.01); *C07C 45/64* (2013.01); *C07C 49/80* (2013.01); *C07F 3/02* (2013.01)

(58) Field of Classification Search
None
See application file for complete search history.

(56) References Cited

FOREIGN PATENT DOCUMENTS

| CN | 102951996 | 3/2013 |
| DE | 3733755 | 4/1989 |
| EP | 0735142 | 10/1996 |
| WO | WO 2013/007767 | 1/2013 |
| WO | WO 2013/024076 | 2/2013 |
| WO | WO 2013/092850 | 6/2013 |
| WO | WO 2013/092856 | 6/2013 |
| WO | WO 2013/092858 | 6/2013 |
| WO | WO 2013/092859 | 6/2013 |
| WO | WO 2013/092943 | 6/2013 |
| WO | WO 2013/113789 | 8/2013 |
| WO | WO 2013/178585 | 12/2013 |
| WO | WO 2014/012811 | 1/2014 |
| WO | WO 2014/026845 | 2/2014 |
| WO | WO 2014/026893 | 2/2014 |
| WO | WO 2014/026928 | 2/2014 |
| WO | WO 2014/108286 | 7/2014 |
| WO | WO 2014/187705 | 11/2014 |
| WO | WO 2014/202589 | 12/2014 |
| WO | WO 2015/003858 | 1/2015 |
| WO | WO 2015/049160 | 4/2015 |
| WO | WO 2015/049360 | 4/2015 |
| WO | WO 2015/055447 | 4/2015 |
| WO | WO 2015/067494 | 5/2015 |
| WO | WO 2015/075087 | 5/2015 |
| WO | WO 2015/082415 | 6/2015 |
| WO | WO 2015/082422 | 6/2015 |
| WO | WO 2015/086689 | 6/2015 |
| WO | WO 2015/091045 | 6/2015 |
| WO | WO 2015/124651 | 8/2015 |
| WO | WO 2015/158518 | 10/2015 |
| WO | WO 2015/158565 | 10/2015 |
| WO | WO 2016/005211 | 1/2016 |
| WO | WO 2016/016369 | 2/2016 |

OTHER PUBLICATIONS

Corey et al., "Dimethyloxosulfonium Methylide (($CH_3)^2SOCH_2$) and Dimethylsulfonium Methylide (($CH_3)^2SCH$). Formation and Application to Organic Synthesis", Journal of the American Chemical Society, 1965, pp. 1354-1364, vol. 87, No. 6.

Kutsuma et al. "A convenient method for a preparation of Oxiranes", Heterocycles, 1977, pp. 397-401, vol. 8.

Lee et al. "Low-Temperature Formation of Functionalized Grignard Reagents from Direct Oxidative Addition of Active Magnesium to Aryl Bromides", The Journal of Organic Chemistry, 2000, pp. 5428-5430, vol. 65.

(Continued)

*Primary Examiner* — Alicia L Otton
(74) *Attorney, Agent, or Firm* — Brinks Gilson & Lione

(57) ABSTRACT

The present invention relates to a process for the preparation of the ketone compounds (IA)

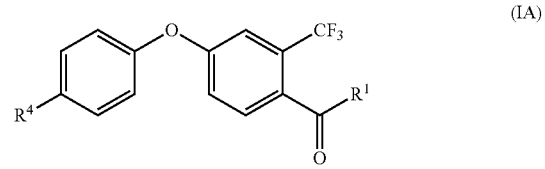

and their use as intermediates for the preparation of triazole fungicides.

10 Claims, No Drawings

(56) References Cited

OTHER PUBLICATIONS

Mosset et al., "Trimethylsulfonium Methylsulfate, A Simple and Efficient Epoxidizing Agent", Synthetic Communications, 1985, pp. 749-757, vol. 15, No. 8.
Tarrant et al., "The Formation and Deamination of Brominated m-Aminobenzotrifluorides", Journal of the American Chemical Society, 1953, pp. 3034-3035, vol. 75, No. 12.
Yu et al. "Synthesis and Fungicidal Evaluation of 2-Arylphenyl Ether-3-(1H-1,2,4-triazol-1-yl)propan-2-ol Derivatives", J. Agric. Food Chem., 2009, pp. 4854-4860, vol. 57.
International Search Report dated Feb. 6, 2015, prepared in International Application No. PCT/EP2014/076839.
International Preliminary Report on Patentability dated Jun. 21, 2016, prepared in International Application No. PCT/EP2014/076839.
European Search Report dated May 14, 2014, prepared in European Application No. 13197924.

PROCESS FOR THE PREPARATION OF SUBSTITUTED PHENOXYPHENYL KETONES

This application is a National Stage application of International Application No. PCT/EP2014/076839, filed Dec. 8, 2014. This application also claims priority under 35 U.S.C. § 119 to European Patent Application No. 14187515.3, filed Oct. 2, 2014 and European Patent Application No. 13197924.7, filed Dec. 18, 2013.

The present invention relates to a process for providing substituted phenoxyphenyl ketones.

Furthermore, the invention relates to intermediates of said process and the use of substituted phenoxyphenyl ketones obtained by the inventive process for the preparation of triazoles.

The substituted phenoxyphenyl ketones provided by the process according to the present invention are valuable intermediate compounds for the synthesis of triazole compounds having pesticidal, in particular fungicidal activity. WO 2013/007767 is directed to fungicidal substituted 1-[4-phenoxy-2-(halogenalkyl)phenyl]-2-(1,2,4-triazol-1-yl) ethanol compounds, that can be synthesized via a respective phenoxyphenyl ketones intermediate compound. WO 2014/108286 (EP 13150663.6; PCT/EP2013/077083) describes an improved process for the synthesis of certain fungicidally active triazole compounds.

The methods known from the literature are sometimes not suitable for the efficient synthesis of substituted phenoxyphenyl ketones because the yield is not sufficient and/or the reaction conditions and parameters such as solvents and/or catalysts and/or the proportion of the reactants and ingredients to each other are not optimal or suitable for an upscale to industrially relevant amounts. Inter alia because said substituted phenoxyphenyl ketones are valuable intermediates for the synthesis of triazole compounds with promising fungicidally activity, there is an ongoing need for improved processes that easily make such intermediates and compounds available.

An object of the present invention was to provide an improved process for the synthesis of substituted phenoxyphenyl ketones (IA) that are valuable intermediates for the preparation of fungicidally active triazole compounds.

It has now surprisingly been found a highly efficient synthesis for the synthesis of substituted phenoxyphenyl ketone compounds of formula (IA), and thus, an efficient synthesis to triazole compounds as active ingredients. The present invention relates thus to a process for the preparation of the ketone compounds (IA)

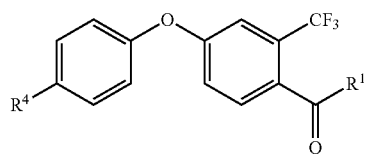

comprising the following steps:
(i) reacting a compound of the formula (III)

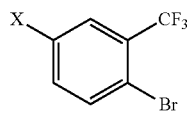

with R'—Mg-Hal (IV) or Mg and $R^1C(=O)Cl$ (V) in the presence of a Cu(I)-catalyst in an amount of 0.005 to 0.065 mole equivalents per 1 mole of compound (III), to result in compounds II

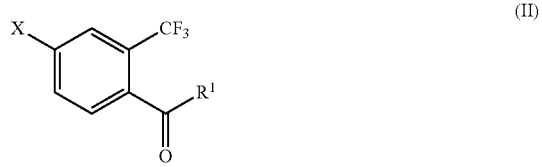

and
(ii) reacting compound (II) as defined in step (i) with a phenol derivative of formula (VI)

in the presence of a base if R" is hydrogen;
wherein the variables are defined as follows:
X is F or Cl;
$R^1$ is $C_1$-$C_6$-alkyl or $C_3$-$C_8$-cycloalkyl; and
$R^4$ is F or Cl;
R' is $C_1$-$C_4$-alkyl or $C_3$-$C_6$-cycloalkyl;
Hal is halogen; and
R" is hydrogen or an alkali metal kation.

In the process step (i) according to the present invention, substituted phenyl compounds of formula (III) are used, wherein X is F or Cl.

The 2-bromo-5-fluoro/chloro-benzotrifluoride of the formula (III) is reacted with the Grignard reagent R'—Mg-Hal (IV) or magnesium (Mg) and the acyl chloride $R^1C(=O)Cl$ (V) in the presence of a Cu(I)catalyst in an amount of 0.005 to 0.065 mol equivalents per 1 mol of compound (III).

According to a preferred embodiment, the Grignard reagent R'—Mg-Hal (IV) is used in the process. R' in the Grignard reagent is $C_1$-$C_4$-alkyl or $C_3$-$C_6$-cycloalkyl, in particular is selected from methyl, ethyl, isopropyl, tert-butyl, sec-butyl and cyclopropyl. Specifically, R' in the Grignard reagent is selected from isopropyl, tert-butyl, sec-butyl and cyclopropyl. In one specific embodiment, R' is isopropyl. In one further embodiment, R' is sec-butyl. Hal stands for halogen, in particular Cl or Br. Also more than one Grignard reagent can be used in the same reaction, such as, for example reagent (IV), wherein Hal is Br together with the respective reagent (having the same R'), wherein Hal is Cl. According to one embodiment, Hal is Cl and R' in the Grignard reagent is selected from isopropyl, tert-butyl, sec-butyl and cyclopropyl. According to a further embodiment, Hal is Br and R' in the Grignard reagent is selected from isopropyl, tert-butyl, sec-butyl and cyclopropyl. In one preferred embodiment, in the inventive process, the Grignard reagent is (iso-propyl)-Mg—Cl or (iso-propyl)-Mg—Br. In one further preferred embodiment, in the inventive process, the Grignard reagent is (sec-butyl)-Mg—Cl or (sec-butyl)-Mg—Br.

Preferably, the Grignard reagent is used in an amount of 1 eq to 2 eq, in particular 1.1 to 1.8 eq, more specifically 1.2 to 1.6 eq, in relation to one equivalent of compound (III). In particular the amounts of 1.3 to 1.5, more particularly 1.2 to 1.4 per mole of compound (III) may be favorable according to the present invention. Usually, the Grignard reagent is used in excess, preferably in slight excess.

One further embodiment relates to the inventive process, wherein Mg is used then forming a Grignard reagent with compound (III) and reacting with compound (V). It can be preferred if Mg is used in an amount slightly less than compound (III). Here, the same details regarding solvents apply.

As generally known to the skilled person, the structure of a Grignard reagent can be described by the so-called Schlenck equilibrium. A Grignard reagent undergoes a solvent-dependent equilibrium between different magnesium compounds. The Schlenck equilibrium for the Grignard reagent used according to the present invention can be schematically illustrated as follows:

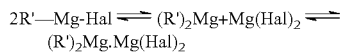

Furthermore, it is known, that solvent molecules, in particular ethers such as diethylether or THF, which are commonly used for reactions with Grignard reagents, can add to the magnesium of the Grignard reagent thereby forming etherates.

Depending on the solvent used in the inventive reaction, solvent molecules may add to the Mg-reagents, thereby forming—in case of the use of ethers—the respective etherates.

For general information regarding structures of Grignard reagents, see also Milton Orchin, Journal of Chemical Education, Volume 66, Number 7, 1999, pp 586 to 588.

According to an embodiment of the inventive process, LiCl is added to the reaction mixture of step (i). According to an alternative, before contacting the Grignard reagent (IV) with the reagents of the inventive process, it is brought together with LiCl, thereby forming an addition product R'MgHal.LiCl ((IV).LiCl). According to this alternative, ((IV).LiCl) is then used in step (i). The use of LiCl together with Grignard reagents is generally known in the art, see for example Angew. Chem. Int. Ed. 2004, 43, 3333 and Angew. Chem. Int. Ed. 2006, 45, 159.

The Grignard reagents (IV) or their addition products with LiCl ((IV).LiCl) are commercially available or can be made according to processes well-known to the skilled person (see Angew. Chem. Int. Ed. 2004, 43, 3333).

The reaction of the educt (III)

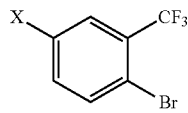

(III)

with a suitable Grignard reagent (IV) or mixture of suitable Grignard reagents may lead to the following specific compounds, wherein "Ar" stands for the respective substituted phenyl unit resulting from compound (III) that has been reacted with the Grignard reagent, as defined herein, in particular, wherein X is F or Cl, namely "Ar1" and "Ar2", respectively. During the reaction different of said Grignard species may occur and also multiple may be formed in parallel:

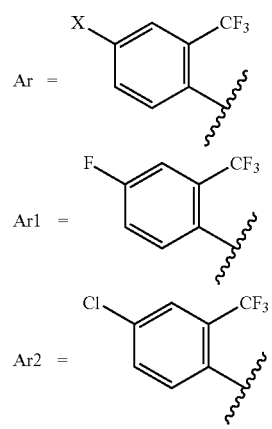

Some of the compounds include solvent molecules such as THF (tetrahydrofurane) as illustrated in the following. It is apparent to the skilled person that also other solvent molecules may be present, depending on the solvent used in the reaction. Also these addition products with solvent molecules are encompassed by the present invention.

Generally, the Grignard species formed during the reaction of (III) with the Grignard reagent (IV) can be depicted as the species "Ga" and "Gb":

Depending on the Grignard reagent (IV) used, Ga or Gb may occur alone or Ga and Gb may be formed both. As outlined above, other Grignard species from the ones detailed below can be formed during the reaction and the different species can convert into one another.

Note 1: "Ar1" or "Ar2", or Cl or Br, having two bonds stands for a three-center-two-electron-bond

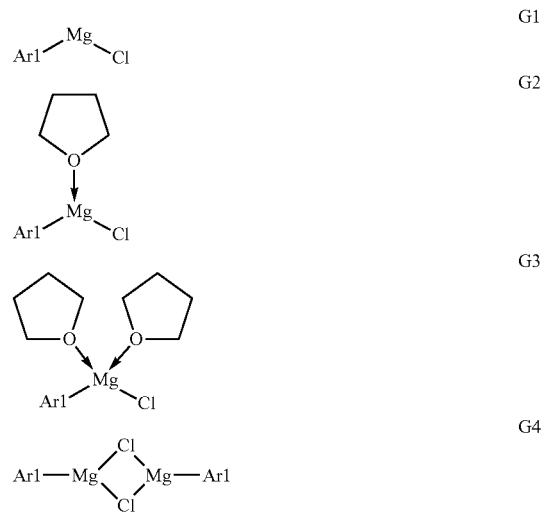

-continued
G5
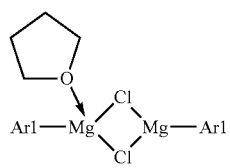
G6
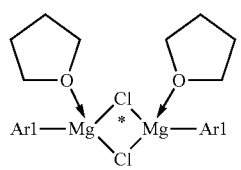
G7
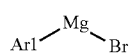
G8
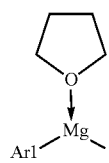
G9
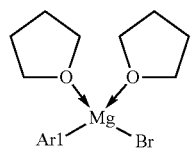
G10
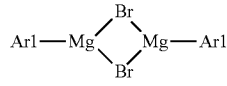
G11
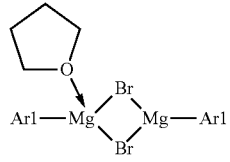
G12
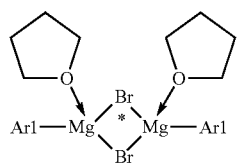
G13
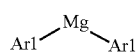
G14
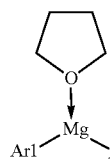
G15
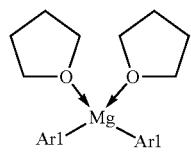
-continued
G16
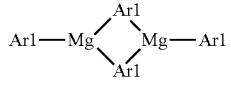
G17
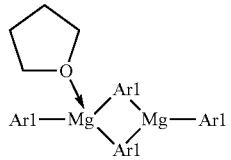
G18
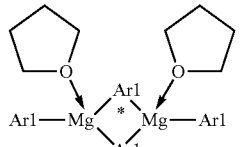
G19
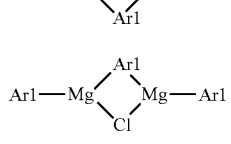
G20
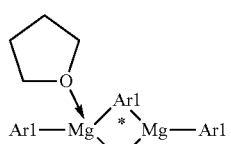
G21
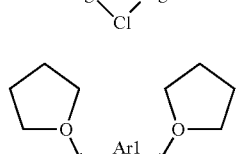
G22
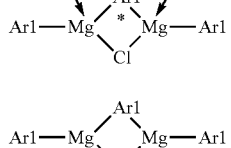
G23
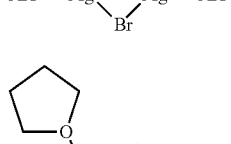
G24
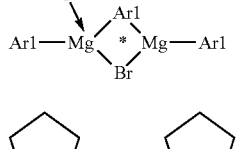
G25
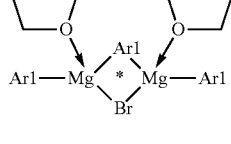
G26
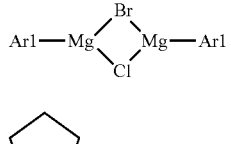

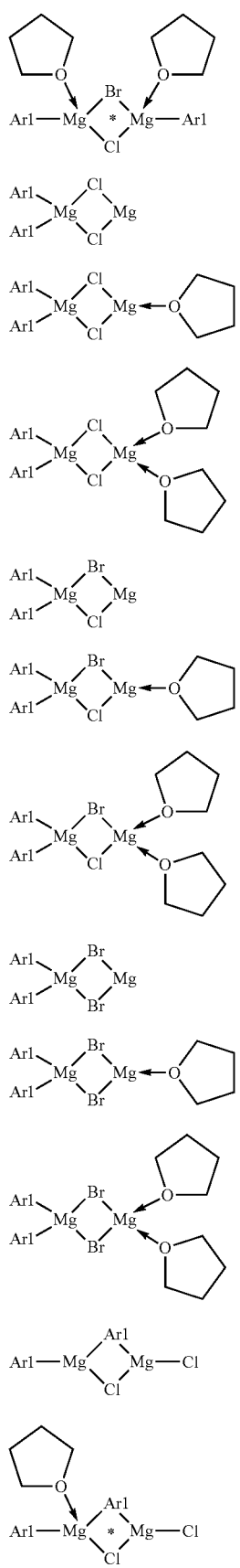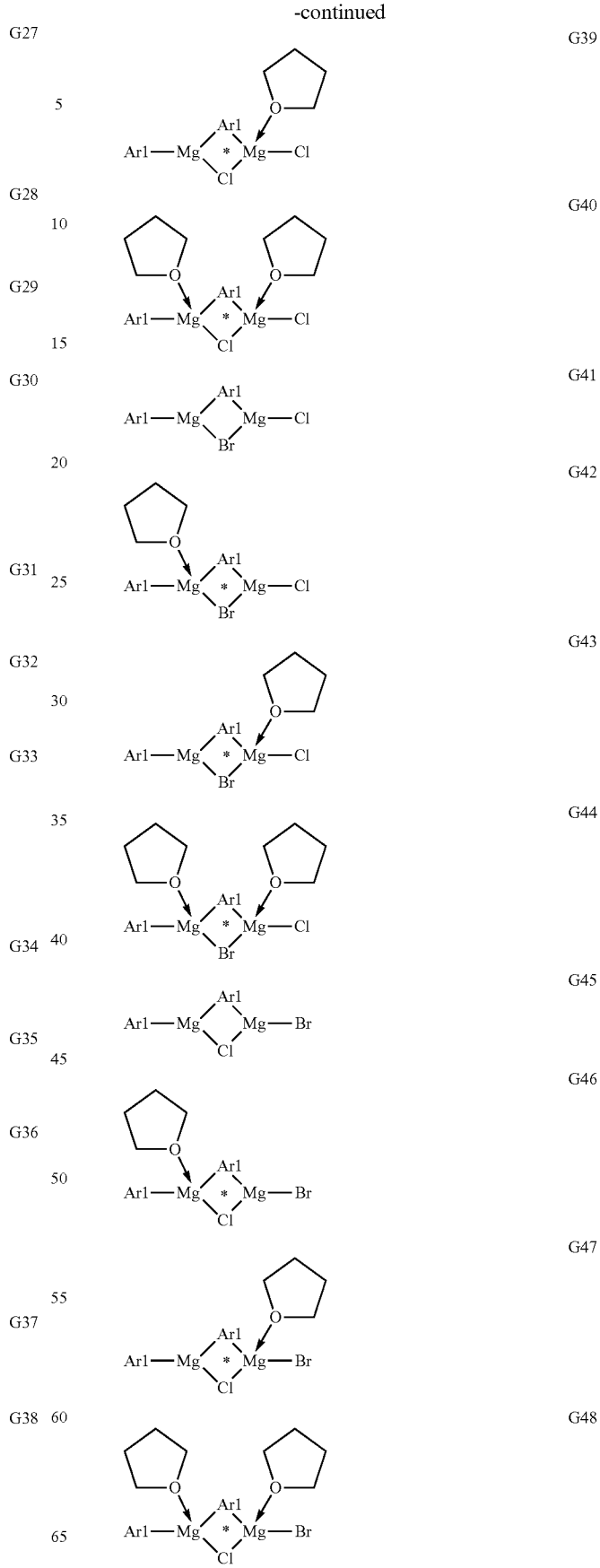

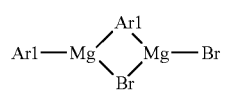
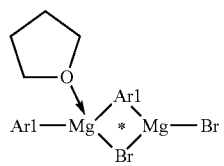
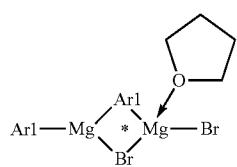
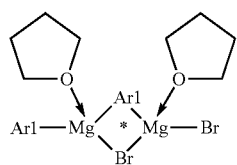
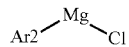
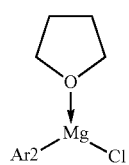
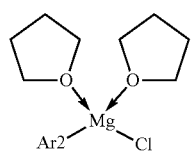
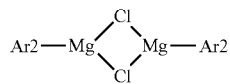
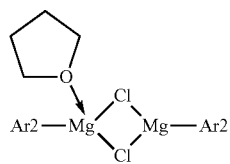
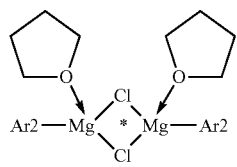
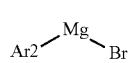
G49
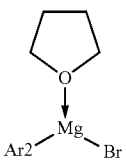
G50
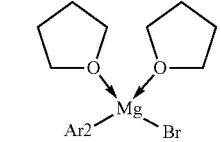
G51
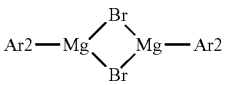
G52
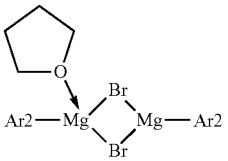
G53
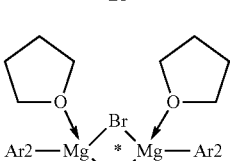
G54
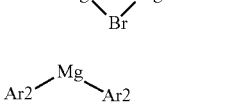
G55
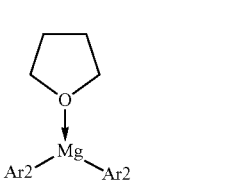
G56
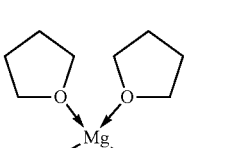
G57
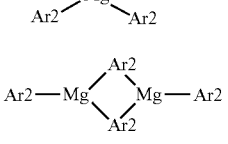
G58
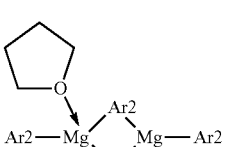
G59
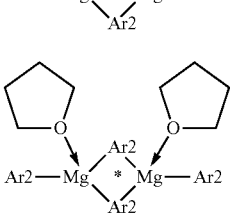
G60
G61
G62
G63
G64
G65
G66
G67
G68
G69
G70

| | |
|---|---|
| 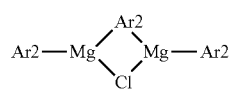 | G71 |
| 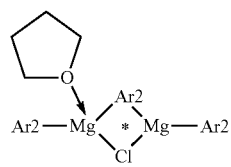 | G72 |
| 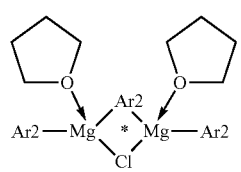 | G73 |
| 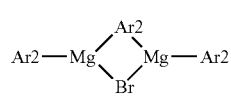 | G74 |
| 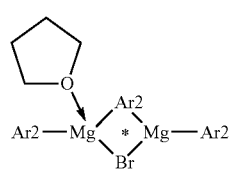 | G75 |
| 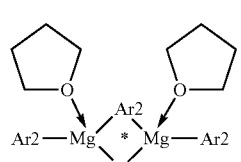 | G76 |
| 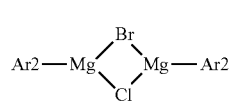 | G77 |
| 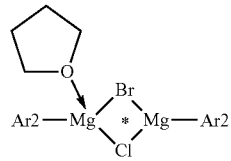 | G78 |
| 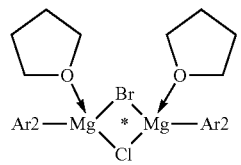 | G79 |
| 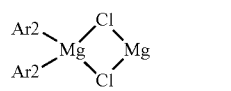 | G80 |
| 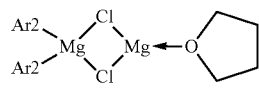 | G81 |
| | |
|---|---|
| 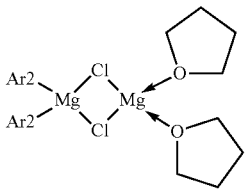 | G82 |
| 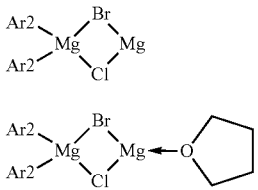 | G83 |
| 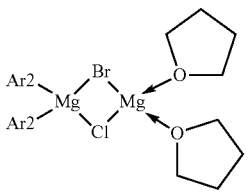 | G84 |
| 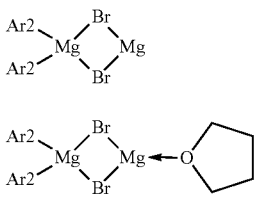 | G85 |
| 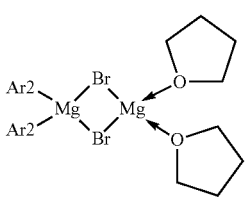 | G86 |
| 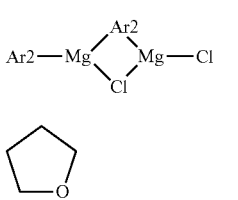 | G87 |
| 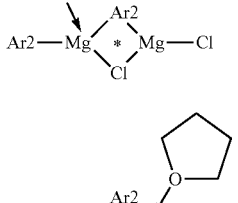 | G88 |
| | G89 |
| 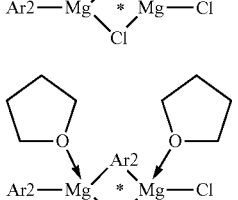 | G90 |
| | G91 |
| | G92 |

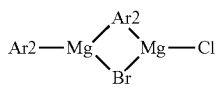

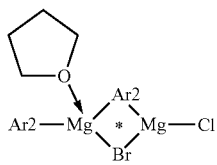

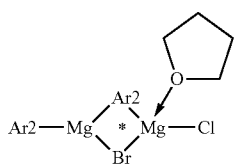

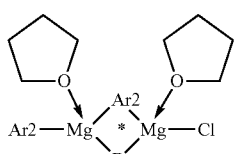

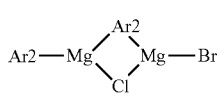

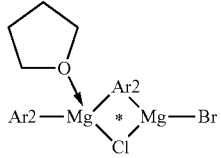

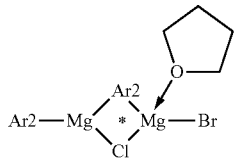

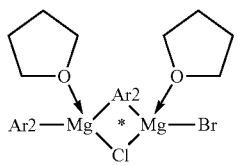

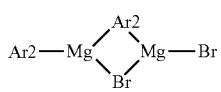

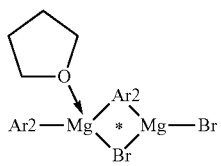

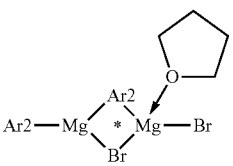

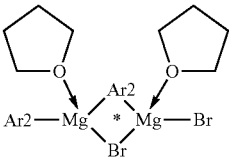

*Note 2: If Mg carries four substituents, it is coordinated tetrahedrally. Thereby, depending on the specific structure, stereoisomers (diastereomers and/or enantiomers) may occur (marked with *). This is demonstrated on a specific example as follows:

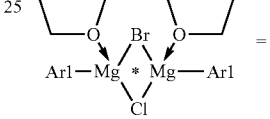

The different magnesium compounds occurring in the inventive process, in particular of the kind as shown above, and possible adducts with solvent molecules are also an aspect of the present invention.

In the carbonyl chloride $R^1C(=O)Cl$ (V), and in the compounds (II), (IA), (IB) and (IC), respectively, $R^1$ is $C_1$-$C_6$-alkyl or $C_3$-$C_8$-cycloalkyl, in particular selected from $CH_3$, $CH(CH_3)_2$ and cyclopropyl.

According to one embodiment, $R^1$ is $C_1$-$C_6$-alkyl, more specifically $C_1$-$C_4$-alkyl, in particular selected from $CH_3$, $C_2H_5$, n-$C_3H_7$, $CH(CH_3)_2$, n-butyl, iso-butyl and tert-butyl, more particularly selected from $CH_3$, $C_2H_5$, $CH(CH_3)_2$ and $C(CH_3)_3$. According to a further embodiment, $R^1$ is $C_3$-$C_8$-cycloalkyl, in particular $C_3$-$C_6$-cycloalkyl, such as $C_3H_5$ (cyclopropyl), $C_4H_7$ (cyclobutyl), cyclopentyl or cyclohexyl. A further embodiment relates to compounds, wherein $R^1$ is $C_3H_5$ (cyclopropyl) or $C_4H_7$ (cyclobutyl), more specifically cyclopropyl.

The carbonyl chloride $R^1C(=O)Cl$ (V) is preferably used in an equimolar amount or in excess compared to the reagent of formula (III). Specifically, the carbonyl chloride is used in an amount of 1 eq to 3 eq, in particular 1.1 to 2.5 eq, more specifically 1.2 to 2 eq, in relation to one equivalent of compound (III). In particular the amounts of 1.3 to 1.8 eq, more specifically 1.4 to 1.6 eq per mole of compound (III) may be favorable according to the present invention. Usually, the carbonyl chloride is used in excess, preferably in slight excess.

The Grignard reagent is added in the manner as is common to the skilled person. In particular, it can be added as solution in an appropriate solvent such as tetrahydrofurane (THF), 1,4-dioxane, diethylether and 2-methyl-tetrahydrofurane.

Examples for appropriate solvents for step (i) of the inventive process are aprotic organic solvents such as for example diethylether, tetrahydrofurane (THF), methyl-tert-butylether (MTBE), toluene, ortho-xylene, meta-xylene, para-xylene and mixtures thereof. Typically, the Grignard reagent is added as solution in THF, 1,4-dioxane, diethylether or 2-methyl-tetrahydrofurane (2-Me-THF), in particular in THF or diethylether, to the reaction vessel or flask containing the reagent (III) and a solvent such as, for example, toluene, MTBE, ortho-xylene, meta-xylene, para-xylene, mesitylene and/or diisopropylether, in particular toluene, MTBE and/or ortho-xylene.

The reaction temperature when adding the Grignard reagent in step (i) is preferably held at a maximum of 50° C., in particular at a maximum of 40° C., more preferably at a maximum of 35° C. Generally, it is preferred to have a reaction temperature of 20° C. to 45° C., in particular room temperature to 45° C., in particular 25° C. to 40° C. In a further embodiment, the temperature is 20° C. to 35° C., specifically 25° C. to 30° C.

In the further course of reaction step (i), the temperature is preferably held at a maximum of 60° C., in particular at a maximum of 50° C., more preferably at a maximum of 45° C. Generally, it is preferred to have a reaction temperature of 30° C. to 50° C., in particular 35° C. to 45° C. In a further embodiment, the temperature is 20° C. to 35° C., specifically 25° C. to 30° C.

An appropriate Cu(I)-catalyst for the inventive process is a Cu(I) salt or Cu(I) oxide, in particular a Cu(I) salt such as Cu(I)Cl or Cu(I)Br or any mixture thereof. According to one specific embodiment, Cu(I)Cl is used. According to the present invention, the Cu(I)-catalyst is present in an amount of 0.005 to 0.065 mol equivalents per 1 mole of compound (III). It is critical to the present invention, that the Cu(I)-catalyst is used in the range of 0.005 to 0.065 mole equivalents per 1 mole of compound (III) defined by the present invention. It has been surprisingly found that lower or higher amounts of the Cu(I)-catalyst are unfavourable due to significantly lower yields. Furthermore, high amounts of the Cu(I)-catalyst lead to increasing problems with phase separations, high costs for the Cu(I)-catalyst and high amounts of undesired toxic Cu(I) and/or Cu(II) in the wastewater, leading in turn to higher process costs for its removal. The present invents avoids these disadvantages and provides a process suitable for industrial upscale.

It may be preferred if 0.005 to 0.055 mol equivalents per 1 mole of compound (III) are used. Also, it may be preferred if 0.055 to 0.045 mol equivalents per 1 mole of compound (III), more specifically 0.005 to 0.04 mol equivalents per 1 mole of compound (III) are used. In particular, the amount of Cu(I)-catalyst is 0.01 to 0.03 mole equivalents per 1 mole of compound III, more particularly 0.015 to 0.025 mole equivalents, even more particularly 0.015 to 0.02, per 1 mole of compound III, specifically 0.018 to 0.023 mole equivalents per 1 mole of compound (III). According to one embodiment, the Cu(I)-catalyst is added in several portions to the reaction mixture, for example in two portions à half of the total amount.

An appropriate course of reaction is such that the Grignard reagent is first reacted with the compound of formula (III) and then, this reaction mixture is added to the carbonyl chloride and a portion of the Cu(I)-catalyst, in particular half of the total amount of the Cu(I) catalyst. After about half of the Grignard mixture has been added to the carbonyl chloride reaction mixture, the remaining amount of Cu(I) is added. According to a further embodiment, the whole amount of Cu(I)-catalyst is added in one portion.

By means of the inventive process step (i), the compounds of formula (II) can be prepared in surprisingly high yields. Preferably, the yields are at least 60%, more preferably 70%, even more preferred at least 75%, even more preferred at least 80%.

After step (i), a work-up of the reaction mixture can be carried out by procedures known in a general manner to the person skilled in the art. Usually, after completion of the reaction, water is added and the organic phase is washed with water, then the solvent is removed from the separated organic phases. Favorably, the so-obtained raw product is directly used in step (ii) of the inventive process. However, the raw product can also be further worked up and/or purified as generally known to the skilled person. If this is deemed appropriate, the reaction mixture is extracted with a suitable organic solvent (for example aromatic hydrocarbons such as toluene and xylenes) and the residue is, if appropriate, purified by recrystallization and/or chromatography.

By means of the inventive process, the compounds of formula (II) can be prepared in surprisingly high yields. Preferably, the yields are at least 60%, more preferably at least 70%, even more preferred at least 75%, even more preferred at least 80%.

According to one embodiment of the invention, in step (i) no $AlCl_3$ is added to the reaction. Consequently, the reaction is carried out in the absence of or at least essentially without $AlCl_3$. In particular at most traces of $AlCl_3$ are present, such as at most 0.0065 mol % $AlCl_3$, for example traces due to impurities of other reagents. It has surprisingly been found that, contrary to what is taught in the prior art, the addition of $AlCl_3$ is unfavourable. It has been found that no addition of $AlCl_3$ according to this embodiment of the invention leads to higher yields.

According to step (ii) of the inventive process, compounds (II) are reacted with a phenol of formula (VI)

(VI)

in the presence of a base.

R" in formula (VI) is hydrogen ((IV) is a substituted phenol) or a alkali metal kation ((VI) is a substituted phenolate). $R^4$ in formula (VI) and formulae (IA), (IB) and (IC), respectively, is F or Cl, in particular Cl.

As described above, compound (II) can be used directly from step (i) without further purification or can be used in purified form.

Examples for appropriate solvents for step (ii) of the inventive process are aprotic organic solvents such as for example dimethyl formamide (DMF), N-methyl pyrrolidone (NMP), Dimethyl imidazolidinone (DMI), toluene, o-xylene, dimethylactamide (DMA) and any mixtures thereof. In particular DMF, NMP, toluene and DMA or any mixtures, more specifically DMF, are particularly suitable.

It may be preferred, if the solvent used in step (ii) contains not more than 3 eq DMF in relation to 1 eq of the phenol of formula (VI), in particular not more than 2.8 eq to 1 eq of the phenol of formula (VI), more specifically not more than 2.6 eq to 1 eq of the phenol of formula (VI). It may be preferred if not more than 2.4, specifically not more than 2.2 eq DMF are used in the process of the invention.

The base used in step (ii) is preferably an inorganic base, according to one embodiment selected from NaOH, KOH, $Na_2CO_3$ and $K_2CO_3$, more specifically from $Na_2CO_3$ and $K_2CO_3$. According to one particular embodiment, $Na_2CO_3$ is used. According to a further particular embodiment, $K_2CO_3$ is used.

The base can be used in solid form or as a solution, e.g. as aqueous solution.

The reagents for step (ii) are preferably added at ambient temperature and the reaction temperature is then elevated, wherein the reaction temperature after the reagents have been added is preferably held at a maximum of 150° C., in particular at a maximum of 140° C., more preferably at a maximum of 130° C. Generally, it is preferred to have a reaction temperature of 20° C. to 135° C., in particular 50° C. to 135° C., more particularly 100° C. to 130° C.

After step (ii), a work-up of the reaction mixture can be carried out by procedures known in a general manner to the person skilled in the art. Generally, water is added and the aqueous phase is extracted with a suitable solvent, e.g. tolene or o-xylene. The raw product obtained after evaporation of the solvent(s) can directly be used in a further step, if desired. However, the raw product can also be further worked up and/or purified as generally known to the skilled person.

According to one embodiment of the invention, after completion of the reaction, most of the solvent (e.g. DMF or toluene) is removed from the reaction mixture, preferably under reduced pressure. Then, a suitable organic solvent, such as, for example, toluene or o-xylene, is added together with water. According to the inventive process, it may be favorable to carry out one to three, preferably two extractions of the aqueous phase.

By means of the inventive process, the compounds of formula (IA) can be prepared in surprisingly high yields. Preferably, the yields of step (ii) are at least 60%, more preferably at least 70%, even more preferred at least 75%, even more preferred at least 80%.

By means of the inventive process, the compounds of formula (IA) can be prepared in surprisingly high yields. Preferably, the yields of steps (i) and (ii) are at least 60%, more preferably at least 70%, even more preferred at least 75%, even more preferred at least 80%.

The starting compounds (III) for the inventive processes can be synthesized as known to the skilled person or are also partly commercially available.

Generally, one undesired side product in the synthesis of compounds (IA), in particular during step (i), that may occur in undesired amounts is the biphenyl compound (Y1)

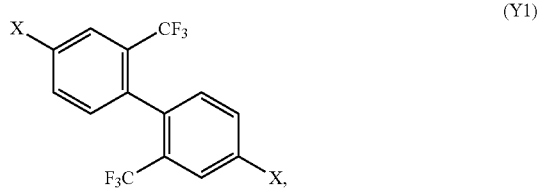

wherein X is F or Cl.

According the reaction conditions of the invention, it is possible to reduce the amount of (Y1). Consequently, according to the inventive process, it is possible to improve the yield of the desired compounds.

Furthermore, the reagents in the inventive process may contain impurities of isomers of compound (III), wherein the Br is attached to another position in the phenol. Accordingly, side products (Y2), (Y3) and/or (Y4) may occur:

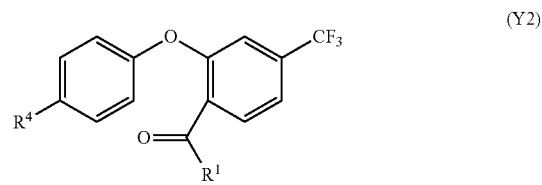

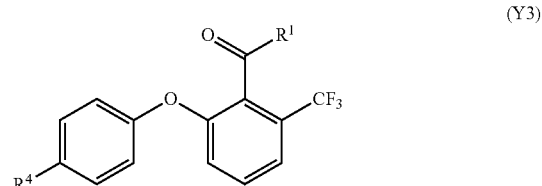

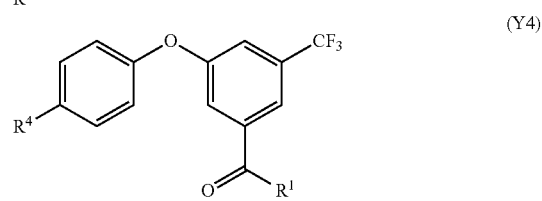

In particular possible side-products (Y2), (Y3) and (Y4), depending on the meaning of variables $R^1$ and $R^4$, are described in Table Y. Therein, every line corresponds to one compound of formula (Y2), (Y3) or (Y4):

TABLE Y

| line | $R^1$ | $R^4$ | Formula |
|---|---|---|---|
| Y-1 | $CH_3$ | Cl | (Y2) |
| Y-2 | $CH_2CH_3$ | Cl | (Y2) |
| Y-3 | $CH_2CH_2CH_3$ | Cl | (Y2) |
| Y-4 | $CH(CH_3)_2$ | Cl | (Y2) |
| Y-5 | $CH_2CH_2CH_2CH_3$ | Cl | (Y2) |
| Y-6 | $C(CH_3)_3$ | Cl | (Y2) |
| Y-7 | $C_3H_5$ (cyclopropyl) | Cl | (Y2) |
| Y-8 | $CH_3$ | Cl | (Y3) |
| Y-9 | $CH_2CH_3$ | Cl | (Y3) |
| Y-10 | $CH_2CH_2CH_3$ | Cl | (Y3) |
| Y-11 | $CH(CH_3)_2$ | Cl | (Y3) |
| Y-12 | $CH_2CH_2CH_2CH_3$ | Cl | (Y3) |
| Y-13 | $C(CH_3)_3$ | Cl | (Y3) |
| Y-14 | $C_3H_5$ (cyclopropyl) | Cl | (Y3) |
| Y-15 | $CH_3$ | Cl | (Y4) |
| Y-16 | $CH_2CH_3$ | Cl | (Y4) |
| Y-17 | $CH_2CH_2CH_3$ | Cl | (Y4) |
| Y-18 | $CH(CH_3)_2$ | Cl | (Y4) |
| Y-19 | $CH_2CH_2CH_2CH_3$ | Cl | (Y4) |
| Y-20 | $C(CH_3)_3$ | Cl | (Y4) |
| Y-21 | $C_3H_5$ (cyclopropyl) | Cl | (Y4) |

The ketone (IA) obtained according to the inventive process can be used as reagent for the synthesis of an oxirane of the formula (IB) that are useful intermediates for the synthesis of triazole active ingredients of formula (IC), that are effective against phytopathogenic fungi. See in particular WO 2013/007767. In EP 13150663.6 favorable process details are outlined. See also JACS 1965, 87, p 1353ff, Heterocycles 8, 1977, p. 397 ff, Synth. Communications, 15, 1985, p 753, J. Agric. Food Chem. 2009, 57, 4854-4860 and DE3733755.

Accordingly, according to a further embodiment of the present invention, following step (ii), the process further comprises the step:
(iii) reacting a ketone of the formula (IA) as defined in step (ii) to result in oxiranes (IB)

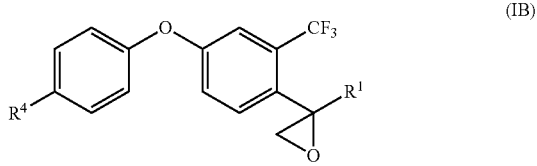

(IB)

wherein $R^1$ and $R^4$ are defined as described and preferably described herein, in particular in the context of formula (IA), (II) and (III).

In this process step, for obtaining an oxirane from the keto group, compound (IA) is preferably reacted with a trimethylsulf(ox)onium halide $((CH_3)_3S^+ (O)Hal^-)$ (VII) or trimethylsulfonium methylsulfate of the formula (VIII) $(CH_3)_3S^+ CH_3SO_4^-$.

According to one embodiment, in the process step (iii), the ketone (IA) is reacted with trimethylsulfonium methylsulfate of the formula VIII $(CH_3)_3S^+ CH_3SO_4^-$, preferably in aqueous solution in the presence of a base.

Step (iii) for the preparation of oxiranes (IB) particularly is as follows:
(iii) reacting an oxo compound of the formula (IA) with trimethylsulfonium methylsulfate of the formula VII

VIII in aqueous solution in the presence of a base, wherein the variables $R^1$, $R^4$ are defined as given and preferably described herein for compounds (IA).

In this process step (iii) using trimethylsulfonium methylsulfate of the formula VIII, preferably, 1 to 4 equivalents, in particular 1.2 to 3.5 eq, more specifically 1.5 to 3.3 eq, of water in relation to one equivalent of compound (IA) are used. It may be favorable, if more than 1.5 eq of water, in particular more than 1.5 eq of water to 4 eq of water, more specifically more than 1.5 eq to 3.5 eq of water, even more particularly more than 1.5 eq water to 2.5 eq water per mole of compound (IA) are used. In particular the ratios of 1.6 to 3.8, more specifically 1.7 to 3.3 eq, more specifically 1.8 to 2.8 eq or 1.9 to 2.5 of water per mole of compound (IA) may be favorable according to the present invention.

The reagent VIII is preferably used in an amount of 1.1 to 2.5, in particular 1.2 to 2, more specifically 1.3 to 1.6 equivalents of VIII per 1 equivalent (mole) of compound (IA).

In general, the reagent of formula VIII can be prepared from dimethylsulfide and dimethylsulfate. According to one embodiment, reagent VIII is prepared in-situ by adding dimethylsulfate to the reaction mixture containing dimethylsulfide. The dimethylsulfide is usually used in excess.

It is preferred to use as reagent VIII an aqueous solution of trimethylsulfonium methylsulfate containing 33 to 37 wt %, preferably 34 to 36 wt %, more specifically 34 to 35.3 wt %, also more specifically 34.3 to 35.9 wt %, of trimethylsulfonium kation.

In particular, the reagent VIII solution contains 33 to 37 wt %, preferably 34 to 36 wt %, more specifically 34 to 35.3 wt %, also more specifically 34.3 to 35.9 wt %, of trimethylsulfonium kation. Accordingly, the amount of trimethylsulfonium-methylsulfate in the reagent, measured as summation of trimethsulfonium-cation and methylsulfate-anion, is about 80 to 90 wt %, preferably about 83 to 88 wt-%, more specifically about 83 to 86 wt-%. The quantification can be, for example, accomplished by means of quantitative NMR-spectroscopie.

The viscosity of the aqueous reagent VIII solution is comparatively low. The solutions are stable at room temparture, in particular at 25° C., and can be stored over a longer time. In particular, the reagent solution does not crystallize out during storage over a longer time, such as several weeks, e.g. up to 12 weeks, at temperatures of 10 to 25° C.

The reagent can be prepared by adding dimethylsulfate to water and dimethylsulfide. Dimethylsulfide is normally used in excess, generally 2 to 8, more preferably 4 to 6, more specifically 4.5 to 5.5, equivalents.

In the preparation of the aqueous solution of reagent VIII, preferably 1.3 to 2.2 eq, more preferably 1.45 to 2.0 eq, water in relation to the dimethylsulfate are used.

Preferably, the temperature of the reaction mixture when adding the dimethylsulfate is room temperature, in particular 25° C. to 40° C.

The aqueous reagent separates as the lower phase and can be further used as such.

The use of the aqueous solution of the reagent VIII has been proven very efficient also for upscaled reaction conditions, since it is stable and since it contains a defined amount of reagent, so that reagent VIII can be easily and precisely dosed to the reaction mixture.

Thus it is a preferred embodiment, if the reagent VIII is added as an aqueous solution of trimethylsulfonium methylsulfate containing 33 to 37 wt %, preferably 34 to 36 wt %, more specifically 34 to 35.3 wt %, also more specifically 34.3 to 35.9 wt % of trimethylsulfonium kation.

The base used in step (iii) is preferably selected from KOH and NaOH. In a preferred embodiment, KOH is used, preferably as solid pellets or flakes. It is preferred if at least 3 equivalents of base, preferably at least 3.2 eq, more specifically at least 3.4 eq per 1 equivalent of compound (IA) are used. It may be preferred if the amount of base is 3 to 6 eq, more specifically 3 to 5 eq per mole of compound (IA).

According to one embodiment of the inventive process, dimethylsulfide is also used as solvent in step (iii). According to a further embodiment, an additional solvent is used. In particular, an aprotic organic solvent is suitable, such as for example diethylether, methyl-tert-butylether, chlorobenzene, xylene or toluene.

The reaction temperature in step (iii) is preferably held at a maximum of 50° C., in particular at a maximum of 45, more preferably at a maximum of 40° C. Generally, it is also preferred to have a reaction temperature of at least 20° C., in particular at least room temperature, in particular at least 25° C. In a further embodiment, the temperature is at least 30° C. It may be preferred if the temperature is at least 35° C.

The oxiranes of formula (IB) can be prepared in high yields. Preferably, the yields are at least 60%, more preferably 70%, even more preferred at least 75%, even more preferred at least 80%.

The order of adding the reactants to the reaction mixture is variable. In one embodiment, the base is added to the solution of compound (IA) and solvent first and then reagent VIII is added. According to another embodiment, the reagent VIII is added first to the solution of compound (IA) and then the base is added. According to a further embodiment, a solution of compound (IA) and the reagent VIII are added simultaneously to the base. In the latter embodiment, the base is preferably suspended in sufficient solvent and is stirred during the addition of the reagents.

For example if side products are contained in the starting material, also the respective undesired side-oxirane products of this process step for obtaining the oxirane (IB) may occur in the reaction. Accordingly, side products (Z2), (Z3) and/or (Z4) may occur:

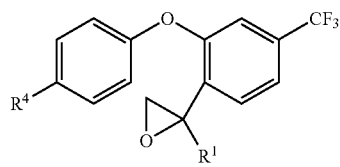
(Z2)

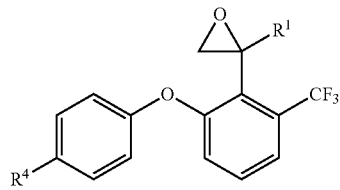
(Z3)

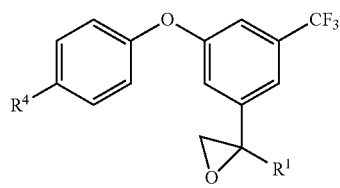
(Z4)

In particular possible side-products (Z2), (Z3) and (Z4), depending on the meaning of variables $R^1$ and $R^4$, are described in Table Z. Therein, every line corresponds to one compound of formula (Z2), (Z3) or (Z4):

TABLE Z

| line | $R^1$ | $R^4$ | Formula |
|---|---|---|---|
| Z-1 | $CH_3$ | Cl | (Z2) |
| Z-2 | $CH_2CH_3$ | Cl | (Z2) |
| Z-3 | $CH_2CH_2CH_3$ | Cl | (Z2) |
| Z-4 | $CH(CH_3)_2$ | Cl | (Z2) |
| Z-5 | $CH_2CH_2CH_2CH_3$ | Cl | (Z2) |
| Z-6 | $C(CH_3)_3$ | Cl | (Z2) |
| Z-7 | $C_3H_5$ (cyclopropyl) | Cl | (Z2) |
| Z-8 | $CH_3$ | Cl | (Z3) |
| Z-9 | $CH_2CH_3$ | Cl | (Z3) |
| Z-10 | $CH_2CH_2CH_3$ | Cl | (Z3) |
| Z-11 | $CH(CH_3)_2$ | Cl | (Z3) |
| Z-12 | $CH_2CH_2CH_2CH_3$ | Cl | (Z3) |
| Z-13 | $C(CH_3)_3$ | Cl | (Z3) |
| Z-14 | $C_3H_5$ (cyclopropyl) | Cl | (Z3) |
| Z-15 | $CH_3$ | Cl | (Z4) |
| Z-16 | $CH_2CH_3$ | Cl | (Z4) |
| Z-17 | $CH_2CH_2CH_3$ | Cl | (Z4) |
| Z-18 | $CH(CH_3)_2$ | Cl | (Z4) |
| Z-19 | $CH_2CH_2CH_2CH_3$ | Cl | (Z4) |
| Z-20 | $C(CH_3)_3$ | Cl | (Z4) |
| Z-21 | $C_3H_5$ (cyclopropyl) | Cl | (Z4) |

The oxiranes (IB) can be further reacted to a triazole of formula (IC)

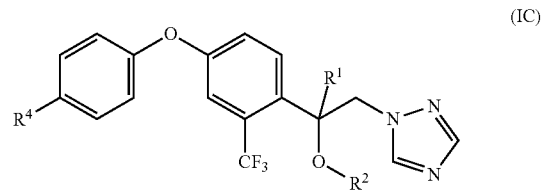
(IC)

wherein the variables $R^1$ and $R^4$ are defined and preferably defined herein, and wherein specific combinations for $R^1$ and $R^4$ are given in Table Y above, and $R^2$ is hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_6$-alkyl, phenyl, phenyl-$C_1$-$C_4$-alkyl, phenyl-$C_2$-$C_4$-alkenyl or phenyl-$C_2$-$C_4$-alkynyl;

wherein the aliphatic moieties of $R^2$ are not further substituted or do carry one, two, three or up to the maximum possible number of identical or different groups $R^{12a}$ which independently are selected from:

$R^{12a}$ halogen, OH, CN, nitro, $C_1$-$C_4$-alkoxy, $C_3$-$C_8$-cycloalkyl, $C_3$-$C_8$-halocycloalkyl and $C_1$-$C_4$-halogenalkoxy;

wherein the cycloalkyl and/or phenyl moieties of $R^2$ are not further substituted or do carry one, two, three, four, five or up to the maximum number of identical or different groups $R^{12b}$ which independently are selected from:

$R^{12b}$ halogen, OH, CN, nitro, $C_1$-$C_4$-alkyl, $C_1$-$C_4$-alkoxy, $C_1$-$C_4$-halogenalkyl, $C_3$-$C_8$-cycloalkyl, $C_3$-$C_8$-halocycloalkyl and $C_1$-$C_4$-halogenalkoxy.

Consequently, according to a further embodiment of the present invention, following step (iii), the process further comprises the step:

(iv) reacting the oxirane of the formula (IB) as defined in step (iii) with 1H-1,2,4-triazole and a base, resulting in compounds of formula (IC), wherein $R^2$ is hydrogen (compounds (IC-1)

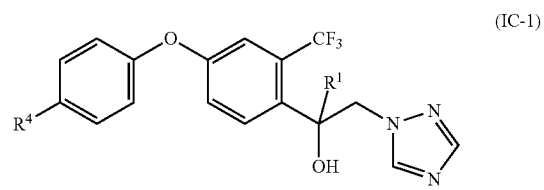
(IC-1)

and, for obtaining compounds (IC), wherein $R^2$ is different from hydrogen (compounds IC-2);

(v) derivatizing the compound of formula (IC-1) as defined in step (iv) under basic conditions with $R^2$-LG, wherein LG is a nucleophilically replaceable leaving group; to result in compounds (IC-2).

Accordingly, a further aspect of the invention relates to a process for the preparation of triazole compounds of the formula (IC)

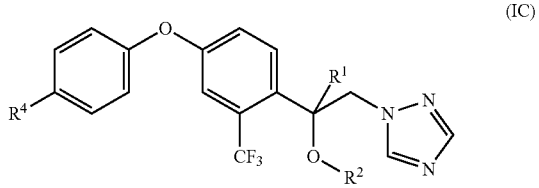

(IC)

comprising the following steps:
(i) as described herein;
(ii) as described herein;
(iii) reacting a ketone of the formula (IA) as defined in step (ii), in particular with a trimethylsulf(ox)onium halide $((CH_3)_3S^+ (O)Hal^-)$ (VII) or trimethylsulfonium methylsulfate of the formula (VIII) $(CH_3)_3S^+ CH_3SO_4^-$, to result in oxiranes (IB); and
(iv) reacting the oxirane (IB) as defined in step (iii) with 1H-1,2,4-triazole in the presence of a base to obtain compounds (IC), wherein $R^2$ is hydrogen (compounds IC-1); and, for obtaining compounds wherein $R^2$ is different from hydrogen:
(v) derivatizing the compound of formula (IC-1) as defined in step (iv) under basic conditions with $R^2$-LG, wherein LG is a nucleophilically replaceable leaving group; to result in compounds (IC-2).

According to one embodiment, the oxirane (IB) is prepared by reaction of the respective oxogroup-containing compound (IA) with trimethylsulf(ox)onium halides $((CH_3)_3S^+ (O)Hal^-)$, preferably trimethylsulfoniumiodide, preferably in the presence of a base such as sodium hydroxide (see also JACS 1965 87 p. 1353).

According to one embodiment, the oxirane (IB) is prepared by reaction of the respective oxogroup-containing compound (IA) with trimethylsulfonium methylsulfate of the formula (VIII) $(CH_3)_3S^+ CH_3SO_4^-$ as detailed above.

LG represents a nucleophilically replaceable leaving group such as halogen, alkylsulfonyl, alkylsulfonyloxy and arylsulfonyloxy, preferably chloro, bromo or iodo, particularly preferably bromo.

According to one embodiment, $R^2$ is selected from $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_4$-alkyl, phenyl, phenyl-$C_1$-$C_4$-alkyl, phenyl-$C_2$-$C_4$-alkenyl and phenyl-$C_2$-$C_4$-alkynyl, wherein the $R^2$ are in each case unsubstituted or are substituted by $R^{12a}$ and/or $R^{12b}$ as defined and preferably defined herein.

According to a further embodiment, $R^2$ is $C_1$-$C_6$-alkyl, in particular $C_1$-$C_4$-alkyl, such as $CH_3$, $C_2H_5$, $CH(CH_3)_2$, $CH_2CH_2CH_3$, $CH_2CH_2CH_2CH_3$, $CH_2CH(CH_3)_2$. A further embodiment relates to compounds, wherein $R^2$ is $C_1$-$C_6$-alkyl, in particular $C_1$-$C_4$-alkyl, that is substituted by one, two or three or up to the maximum possible number of identical or different groups $R^{12a}$, as defined and preferably defined herein. According to a specific embodiment thereof, $R^2$ is $C_1$-$C_6$-haloalkyl, in particular $C_1$-$C_4$-haloalkyl, more particularly $C_1$-$C_2$-haloalkyl. According to a further specific embodiment thereof, $R^2$ is $C_1$-$C_4$-alkoxy-$C_1$-$C_6$-alkyl, in particular $C_1$-$C_4$-alkoxy-$C_1$-$C_4$-alkyl, such as $CH_2OCH_3$ or $CH_2CH_2OCH_3$. According to still a further specific embodiment thereof, $R^2$ is hydroxy-$C_1$-$C_6$-alkyl, in particular hydroxyl-$C_1$-$C_4$-alkyl, such as $CH_2CH_2OH$.

According to still another embodiment, $R^2$ is $C_3$-$C_8$-cycloalkyl-$C_1$-$C_6$-alkyl, in particular $C_3$-$C_6$-cycloalkyl-$C_1$-$C_4$-alkyl. A further embodiment relates to compounds, wherein $R^2$ is $C_3$-$C_8$-cycloalkyl-$C_1$-$C_6$-alkyl, in particular $C_3$-$C_6$-cycloalkyl-$C_1$-$C_4$-alkyl, more particularly $C_3$-$C_6$-cycloalkyl-$C_1$-$C_2$-alkyl, that is substituted by one, two or three or up to the maximum possible number of identical or different groups $R^{12a}$ in the alkyl moiety and/or substituted by one, two, three four or five or up to the maximum possible number of identical or different groups $R^{12b}$ in the cycloalkyl moiety. $R^{12a}$ and $R^{12b}$ are in each case as defined and preferably defined herein.

According to another embodiment, $R^2$ is $C_2$-$C_6$-alkenyl, in particular $C_2$-$C_4$-alkenyl, such as $CH_2CH=CH_2$, $CH_2C(CH_3)=CH_2$ or $CH_2CH=CHCH_3$. A further embodiment relates to compounds, wherein $R^2$ is $C_2$-$C_6$-alkenyl, in particular $C_2$-$C_4$-alkenyl, that is substituted by one, two or three or up to the maximum possible number of identical or different groups $R^{12a}$ as defined and preferably defined herein. According to a specific embodiment thereof, $R^2$ is $C_2$-$C_6$-haloalkenyl, in particular $C_2$-$C_4$-haloalkenyl, such as $CH_2C(Cl)=CH_2$ and $CH_2C(H)=CHCl$. According to a further specific embodiment thereof, $R^2$ is $C_3$-$C_8$-cycloalkyl-$C_2$-$C_6$-alkenyl or $C_3$-$C_8$-halocycloalkyl-$C_2$-$C_6$-alkenyl, in particular $C_3$-$C_6$-cycloalkyl-$C_2$-$C_4$-alkenyl or $C_3$-$C_6$-halocycloalkyl-$C_2$-$C_4$-alkenyl.

According to still another embodiment, $R^2$ is $C_2$-$C_6$-alkynyl, in particular $C_2$-$C_4$-alkynyl, such as $CH_2C\equiv CH$ or $CH_2C\equiv CCH_3$. A further embodiment relates to compounds, wherein $R^2$ is $C_2$-$C_6$-alkynyl, in particular $C_2$-$C_4$-alkynyl, that is substituted by one, two or three or up to the maximum possible number of identical or different groups $R^{12a}$, as defined and preferably defined herein. According to a specific embodiment thereof, $R^2$ is $C_2$-$C_6$-haloalkynyl, in particular $C_2$-$C_4$-haloalkynyl. According to a further specific embodiment thereof, $R^2$ is $C_3$-$C_8$-cycloalkyl-$C_2$-$C_6$-alkynyl or $C_3$-$C_8$-halocycloalkyl-$C_2$-$C_6$-alkynyl, in particular $C_3$-$C_6$-cycloalkyl-$C_2$-$C_4$-alkynyl or $C_3$-$C_6$-halocycloalkyl-$C_2$-$C_4$-alkynyl.

According to still another embodiment, $R^2$ is phenyl-$C_1$-$C_4$-alkyl, in particular phenyl-$C_1$-$C_2$-alkyl, such as benzyl, wherein the alkyl moiety in each case is unsubstituted or carries one, two or three $R^{12a}$ as defined and preferably defined herein, in particular selected from halogen, in particular F and Cl, $C_1$-$C_4$-alkoxy, in particular $OCH_3$, and CN, and wherein the phenyl in each case is unsubstituted or carries one, two or three $R^{12b}$ as defined and preferably defined herein, in particular selected from halogen, in particular Cl and F, $C_1$-$C_4$-alkoxy, in particular $OCH_3$, $C_1$-$C_4$-alkyl, in particular $CH_3$ or $C_2H_5$, and CN.

According to still another embodiment, $R^2$ is phenyl-$C_2$-$C_4$-alkenyl, in particular phenyl-$C_2$-$C_3$-alkenyl, such as phenylethenyl, wherein the alkenyl moiety in each case is unsubstituted or carries one, two or three $R^{12a}$ as defined and preferably defined herein, in particular selected from halogen, in particular F and Cl, $C_1$-$C_4$-alkoxy, in particular $OCH_3$, and CN, and wherein the phenyl in each case is unsubstituted or carries one, two or three $R^{12b}$ as defined and preferably defined herein, in particular selected from halogen, in particular Cl and F, $C_1$-$C_4$-alkoxy, in particular $OCH_3$, $C_1$-$C_4$-alkyl, in particular $CH_3$ or $C_2H_5$, and CN.

According to still another embodiment, $R^2$ is phenyl-$C_2$-$C_4$-alkynyl, in particular phenyl-$C_2$-$C_3$-alkynyl, such as phenylethinyl, wherein the alkynyl moiety in each case is unsubstituted or carries one, two or three $R^{12a}$, as defined and preferably defined herein, in particular selected from halogen, in particular F and Cl, $C_1$-$C_4$-alkoxy, in particular $OCH_3$, and CN, and wherein the phenyl in each case is unsubstituted or carries one, two or three $R^{12b}$ as defined and preferably defined herein, in particular selected from halogen, in particular Cl and F, $C_1$-$C_4$-alkoxy, in particular $OCH_3$, $C_1$-$C_4$-alkyl, in particular $CH_3$ or $C_2H_5$, and CN.

According to still another embodiment, $R^2$ is $C_3$-$C_8$-cycloalkyl, in particular $C_3$-$C_6$-cycloalkyl, such as $C_3H_5$ (cyclopropyl), $C_4H_7$ (cyclobutyl), cyclopentyl or cyclohexyl. A further embodiment relates to compounds, wherein $R^2$ is $C_3$-$C_8$-cycloalkyl, in particular $C_3$-$C_6$-cycloalkyl, such as $C_3H_5$ (cyclopropyl) or $C_4H_7$ (cyclobutyl), that is substituted by one, two, three four or five or up to the maximum possible number of identical or different groups $R^{12b}$ as defined and preferably defined herein. According to a specific embodiment thereof, $R^2$ is $C_3$-$C_8$-halocycloalkyl, in particular $C_3$-$C_6$-halocycloalkyl, such as halocyclopropyl, in particular 1-F-cyclopropyl or 1-Cl-cyclopropyl. According to a further specific embodiment thereof, $R^2$ is $C_3$-$C_8$-cycloalkyl-$C_3$-$C_8$-cycloalkyl, in particular $C_3$-$C_6$-cycloalkyl-$C_3$-$C_6$-cycloalkyl, wherein each of said cycloalkyl-cycloalkyl moieties is unsubstituted or carries one, two or three $R^{12b}$ as defined and preferably defined herein.

According to still another embodiment, $R^2$ is phenyl, wherein the phenyl is unsubstituted or carries one, two, three, four or five independently selected $R^{12b}$ as defined and preferably defined herein, in particular selected from halogen, in particular Cl and F, $C_1$-$C_4$-alkoxy, in particular $OCH_3$, $C_1$-$C_4$-alkyl, in particular $CH_3$ or $C_2H_5$, and CN.

In a further embodiment of the invention, $R^2$ is selected from $C_1$-$C_6$-alkyl, $C_2$-$C_6$-alkenyl and $C_2$-$C_6$-alkynyl, wherein the $R^2$ are in each case unsubstituted or are substituted by $R^{12a}$ and/or $R^{12b}$ as defined and preferably defined herein. In each case, the substituents may also have the preferred meanings for the respective substituent as defined above.

$R^{12a}$ according to the invention is independently selected from halogen, OH, CN, nitro, $C_1$-$C_4$-alkoxy, $C_3$-$C_8$-cycloalkyl, $C_3$-$C_8$-halocycloalkyl and $C_1$-$C_4$-halogenalkoxy. According to one embodiment $R^{12a}$ is independently selected from halogen, OH, CN, $C_1$-$C_2$-alkoxy, $C_3$-$C_6$-cycloalkyl, $C_3$-$C_6$-halocycloalkyl and $C_1$-$C_2$-halogenalkoxy. Specifically, $R^{12a}$ is independently selected from F, Cl, OH, CN, $C_1$-$C_2$-alkoxy, cyclopropyl, 1-F-cyclopropyl, 1-Cl-cyclopropyl and $C_1$-$C_2$-halogenalkoxy.

$R^{12b}$ according to the invention is independently selected from halogen, OH, CN, nitro, $C_1$-$C_4$-alkyl, $C_1$-$C_4$-alkoxy, $C_1$-$C_4$-halogenalkyl, $C_3$-$C_8$-cycloalkyl, $C_3$-$C_8$-halocycloalkyl and $C_1$-$C_4$-halogenalkoxy. According to one embodiment $R^{12b}$ is independently selected from halogen, CN, nitro, $C_1$-$C_2$-alkyl, $C_1$-$C_2$-alkoxy, $C_1$-$C_2$-halogenalkyl, $C_3$-$C_6$-cycloalkyl, $C_3$-$C_6$-halocycloalkyl and $C_1$-$C_2$-halogenalkoxy. Specifically, $R^{12b}$ is independently selected from F, Cl, OH, CN, nitro, $CH_3$, $OCH_3$, cyclopropyl, 1-F-cyclopropyl, 1-Cl-cyclopropyl and halogenmethoxy.

For example if side products are contained in the starting material, also the respective undesired triazole side-products may occur in the reaction:

Accordingly, side products (T2), (T3) and/or (T4) may occur:

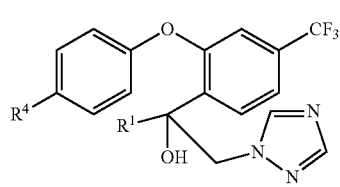

(T2)

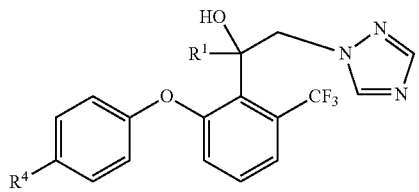

(T3)

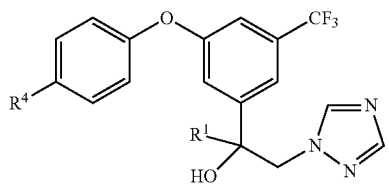

(T4)

In particular possible side-products (T2), (T3) and (T4), depending on the meaning of variables $R^1$ and $R^4$, are described in Table T. Therein, every line corresponds to one compound of formula (T2), (T3) or (T4):

TABLE T

| line | $R^1$ | $R^4$ | Formula |
|------|-------|-------|---------|
| T-1 | $CH_3$ | Cl | (T2) |
| T-2 | $CH_2CH_3$ | Cl | (T2) |
| T-3 | $CH_2CH_2CH_3$ | Cl | (T2) |
| T-4 | $CH(CH_3)_2$ | Cl | (T2) |
| T-5 | $CH_2CH_2CH_2CH_3$ | Cl | (T2) |
| T-6 | $C(CH_3)_3$ | Cl | (T2) |
| T-7 | $C_3H_5$ (cyclopropyl) | Cl | (T2) |
| T-8 | $CH_3$ | Cl | (T3) |
| T-9 | $CH_2CH_3$ | Cl | (T3) |
| T-10 | $CH_2CH_2CH_3$ | Cl | (T3) |
| T-11 | $CH(CH_3)_2$ | Cl | (T3) |
| T-12 | $CH_2CH_2CH_2CH_3$ | Cl | (T3) |
| T-13 | $C(CH_3)_3$ | Cl | (T3) |
| T-14 | $C_3H_5$ (cyclopropyl) | Cl | (T3) |
| T-15 | $CH_3$ | Cl | (T4) |
| T-16 | $CH_2CH_3$ | Cl | (T4) |
| T-17 | $CH_2CH_2CH_3$ | Cl | (T4) |
| T-18 | $CH(CH_3)_2$ | Cl | (T4) |
| T-19 | $CH_2CH_2CH_2CH_3$ | Cl | (T4) |
| T-20 | $C(CH_3)_3$ | Cl | (T4) |
| T-21 | $C_3H_5$ (cyclopropyl) | Cl | (T4) |

An undesired side-product of the triazole reaction is also the symmetric triazole

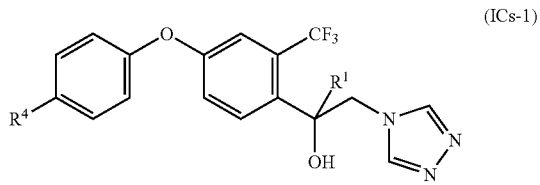

(ICs-1)

Accordingly, the respective symmetric side products of (T2), (T3) and/or (T4) may occur, named (Ts2), (Ts3) and (Ts4), respectively:

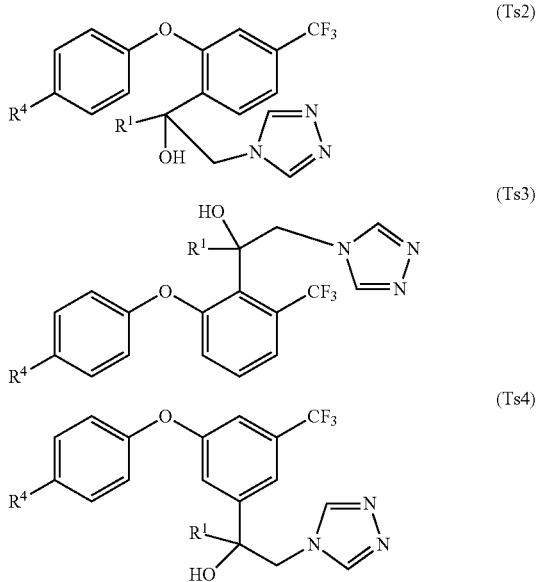

In particular possible side-products (Ts2), (Ts3) and (Ts4), depending on the meaning of variables $R^1$ and $R^4$, are described in Table Ts. Therein, every line corresponds to one compound of formula (Ts2), (Ts3) or (Ts4):

TABLE Ts

| line | $R^1$ | $R^4$ | Formula |
|---|---|---|---|
| Ts-1 | CH₃ | Cl | (Ts2) |
| Ts-2 | CH₂CH₃ | Cl | (Ts2) |
| Ts-3 | CH₂CH₂CH₃ | Cl | (Ts2) |
| Ts-4 | CH(CH₃)₂ | Cl | (Ts2) |
| Ts-5 | CH₂CH₂CH₂CH₃ | Cl | (Ts2) |
| Ts-6 | C(CH₃)₃ | Cl | (Ts2) |
| Ts-7 | C₃H₅ (cyclopropyl) | Cl | (Ts2) |
| Ts-8 | CH₃ | Cl | (Ts3) |
| Ts-9 | CH₂CH₃ | Cl | (Ts3) |
| Ts-10 | CH₂CH₂CH₃ | Cl | (Ts3) |
| Ts-11 | CH(CH₃)₂ | Cl | (Ts3) |
| Ts-12 | CH₂CH₂CH₂CH₃ | Cl | (Ts3) |
| Ts-13 | C(CH₃)₃ | Cl | (Ts3) |
| Ts-14 | C₃H₅ (cyclopropyl) | Cl | (Ts3) |
| Ts-15 | CH₃ | Cl | (Ts4) |
| Ts-16 | CH₂CH₃ | Cl | (Ts4) |
| Ts-17 | CH₂CH₂CH₃ | Cl | (Ts4) |
| Ts-18 | CH(CH₃)₂ | Cl | (Ts4) |
| Ts-19 | CH₂CH₂CH₂CH₃ | Cl | (Ts4) |
| Ts-20 | C(CH₃)₃ | Cl | (Ts4) |
| Ts-21 | C₃H₅ (cyclopropyl) | Cl | (Ts4) |

In one embodiment of the invention, the process (iv) is as follows:
(iv) reacting the oxirane (IB) as defined in step (iii) with 1H-1,2,4-triazole and an inorganic base to obtain compounds (IC), wherein $R^2$ is hydrogen (compounds IC-1).

The inorganic base used in step (iv) is preferably selected from NaOH, KOH, Na₂CO₃ and K₂CO₃, more specifically from NaOH and KOH. According to one embodiment, NaOH is used. According to a further embodiment, KOH is used.

According to a specific embodiment, the sodium salt of 1H-1,2,4-triazole as a base is used, wherein said sodium salt is prepared using triazole and a base preferably selected from NaOH, NaH and Na-alcoholates. See also DE 3042302.

The amount of base used in step (iv) is preferably equal to or less than 1 eq, in particular less than 1 eq, more preferably equal to or less than 0.8 eq, even more preferably equal to or less than 0.6 equivalents per 1 equivalent of compound (IB). Also preferred are amounts of base being equal to or less than 0.4 equivalents, in particular equal to or less than 0.2 equivalents, specifically equal to or less than 0.1 eq per 1 equivalent of compound (IB). Preferably, at least 0.1 eq, more preferably at least 0.2 equivalents, in particular at least 0.3, more specifically at least 0.4 eq base per 1 equivalent of compound (IB) are used.

Higher yields of compounds (IC-1) can be achieved, if less than 1 eq of base is used in relation to the compound (IB). In specific embodiments thereof, NaOH is used in as base, preferably in an amount as given above, in particular in an amount of 0.1 to 0.55 eq in relation to the oxirane of formula (IB).

In order to have preferably low reaction times, temperatures of at least 100° C., more preferably at least 110° C., in particular at least 120° C. are favorable. It is also an embodiment to reflux the reaction mixture. Preferably, the reaction temperature is not higher than 150° C., in particular not higher than 140° C. Specifically, a reaction temperature of 120° C. to 140° C. is used.

The amount of 1H-1,2,4-triazole used in step (iv) generally is at least 1 eq per mole of oxirane (IB). According to one embodiment, the 1H-1,2,4-triazole is used in excess in relation to the oxirane (IB). Preferred are more than 1 eq to 2 eq, more preferably more than 1 eq to 1.8 eq, even more preferred more than 1 eq to 1.6 eq. Mostly for economic reason, it can be preferred to use at least 1.1 eq, specifically 1.15 eq, to 1.5 eq of triazole in relation to oxirane (IB).

The solvent used in step (iv) is preferably selected from dimethylformamide, dimethylacetamide, N-methylpyrrolidone. Most preferred is dimethylformamide.

According to one preferred embodiment, the compounds (IC-1) resulting from step (iv) are crystallized from a suitable solvent such as, for example toluene, an aliphatic alcohol, acetonitrile, ethyl acetate and/or cyclohexane, in particular toluene and/or an aliphatic alcohol.

In particular, the aliphatic alcohol is selected from methanol, ethanol, n-propanol, iso-propanol, n-butanol, isobutanol or any mixture thereof. In particular, the aliphatic alcohol is selected from methanol and ethanol.

Generally, for the crystallizing step, the solvent, in particular dimethylformide as described above, is firstly evaporated in large part, preferably under reduced pressure. Preferably, at least 55% of the solvent, more preferably at least 60% of the sovent, more specifically at least 70% of the solvent are removed. Specifically, it may be preferred, if at least 80%, more specifically at least 90% of the solvent, such as DMF, are removed The solvent can then be recycled to be used again in the process step (iv), if necessary after it has been further rectificated before.

Then, water and the respective suitable solvent such as an ether, for example diethylether, diisopropylether, methyl-tert-butylether (MTBE), methylenechlorid and/or toluene, in particular toluene, are added. Also ethyl acetate can be appropriate as solvent. The product (IC-1) is then preferably obtained by crystallization directly from the concentrated, e.g. toluene-reaction mixture. Also preferred and suitable according to the invention is the change of solvent to e.g. methanole or ethanole (see above) for the crystallization of the products.

According to one embodiment, seed crystals are added for the crystallization step.

By using the crystallizing step, in particular when carrying out the process steps (iv) the formation of the undesired symmetric triazole (ICs-1) as described above can be reduced to equal or less than 10%, more preferably equal or less than 8%, even more preferably equal or less than 5%, even more preferably equal or less than 2%.

Preferably, the ratio of isolated compound (IC-1) to the symmetric triazole (ICs-1) is at least 20:1, more preferably at least 30:1, even more preferably 50:1, more specifically 70:1. In particular, the ratio of compound (IC-1) to (ICs-1) is at least 30:1.

Also other methods of further reacting the oxiranes (IB) to end products (IC) can be carried out.

For example, the epoxide ring of compounds (IB) may be cleaved by reaction with alcohols $R^2OH$ preferably under acidic conditions to result in compounds IX:

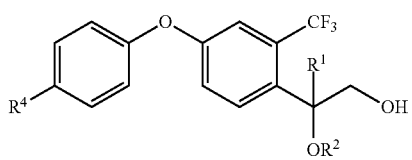

Thereafter, the resulting compounds IX are reacted with halogenating agents or sulfonating agents such as $PBr_3$, $PCl_3$ mesyl chloride, tosyl chloride or thionyl chloride, to obtain compounds X wherein LG' is a nucleophilically replaceable leaving group such as halogen, alkylsulfonyl, alkylsulfonyloxy and arylsulfonyloxy, preferably chloro, bromo or iodo, particularly preferably bromo or alkylsulfonyl. Then compounds X are reacted with 1H-1,2,4-triazole to obtain compounds IC as known in the art and/or described above:

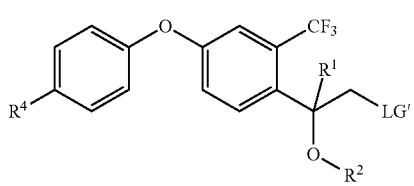

For obtaining compounds of formula IC, wherein the alcohol group is derivatized into an ether group to result in compounds of formula IC-2, wherein the variables are defined above, the following step can be carried out:

(v) derivatizing the compound of formula (IC-1) as defined in step (iv) under basic conditions with $R^2$-LG, wherein LG is a nucleophilically replaceable leaving group; to result in compounds (IC-2).

LG represents a nucleophilically replaceable leaving group such as halogen, alkylsulfonyl, alkylsulfonyloxy and arylsulfonyloxy, preferably chloro, bromo or iodo, particularly preferably bromo. Preferably a base is use in step (iii) such as for example, NaH.

Suitable solvents are for example ethers, in particular cyclic ethers. Possible solvents are for example tetrahydrofuran (THF), 2-methyl-tetrahydrofuran (2-Me-THF), diethyl ether, TBME (tert-butyl methyl ether), CPME (cyclopentyl methyl ether), DME (1,2-dimethoxyethane) and 1,4-dioxane. Further solvents that may be suitable are, for example, diisopropyl ether, di-n-butyl ether and/or diglyme. Often, the use of THF or 2-methyl-THF is particularly suitable. Furthermore, it may also be suitable to use combinations of two or more different solvents, such as for example any combination of the solvents listed above or any one of the listed ethers with aliphatic hydrocarbons like n-hexane, heptane or aromatic hydrocarbons like toluene or xylenes.

The skilled person is familiar with the reaction in step (v) and may vary the reaction conditions analogously to known syntheses.

In one embodiment, a triazole compound of the formula IC is obtained by

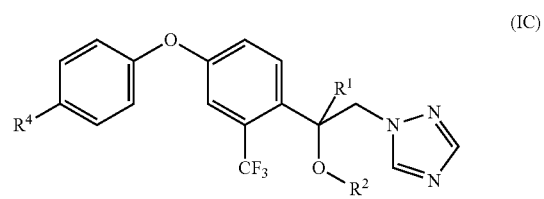

(iv-a) reacting an oxirane of the formula (IB) as defined herein; with 1H-1,2,4-triazole and an inorganic base, wherein less than 1 equivalent of said base is used per 1 equivalent of compound (IB), resulting in compounds of formula (IC).

For obtaining compounds of formula (IC-2), wherein the alcohol group is derivatized (resulting in "$OR^2$", see above), the above derivatizing step can be carried out.

In the definitions of the variables given herein, collective terms are used which are generally representative for the substituents in question. The term "$C_n$-$C_m$" indicates the number of carbon atoms possible in each case in the substituent or substituent moiety in question.

The term "halogen" refers to fluorine, chlorine, bromine and iodine.

The term "$C_1$-$C_6$-alkyl" refers to a straight-chained or branched saturated hydrocarbon group having 1 to 6 carbon atoms, e.g. methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Likewise, the term "$C_2$-$C_4$-alkyl" refers to a straight-chained or branched alkyl group having 2 to 4 carbon atoms, such as ethyl, propyl (n-propyl), 1-methylethyl (iso-propoyl), butyl, 1-methylpropyl (sec.-butyl), 2-methylpropyl (iso-butyl), 1,1-dimethylethyl (tert.-butyl).

The term "$C_3$-$C_8$-cycloalkyl" refers to monocyclic saturated hydrocarbon radicals having 3 to 8 carbon ring members, such as cyclopropyl, cyclobutyl, cyclopentyl, cyclohexyl, cycloheptyl or cyclooctyl.

The meanings and preferred meanings described herein for the variables $R^1$, $R^2$, $R^4$, X, R' and R'' apply to all compounds and the precursors of the compounds and side products in any of the process steps detailed herein.

$R^4$ according to the present invention is independently selected from F and Cl. Specifically, the following compounds IC.1 to IC.7 can advantageously be prepared using the process according to the present invention:

| | |
|---|---|
| compound IC.1 | 2-[4-(4-chlorophenoxy)-2-(trifluoromethyl)phenyl]-1-(1,2,4-triazol-1-yl)propan-2-ol; |
| compound IC.2 | 1-[4-(4-chlorophenoxy)-2-(trifluoromethyl)phenyl]-1-cyclopropyl-2-(1,2,4-triazol-1-yl)ethanol; |
| compound IC.3 | 2-[4-(4-chlorophenoxy)-2-(trifluoromethyl)phenyl]-3-methyl-1-(1,2,4-triazol-1-yl)butan-2-ol; |
| compound IC.4 | 2-[4-(4-chlorophenoxy)-2-(trifluoromethyl)phenyl]-1-(1,2,4-triazol-1-yl)butan-2-ol; |
| compound IC.5 | 1-[2-[4-(4-chlorophenoxy)-2-(trifluoromethyl)phenyl]-2-methoxy-propyl]-1,2,4-triazole; |
| compound IC.6 | 1-[2-[4-(4-chlorophenoxy)-2-(trifluoromethyl)phenyl]-2-cyclopropyl-2-methoxy-ethyl]-1,2,4-triazole; |
| compound IC.7 | 1-[2-[4-(4-chlorophenoxy)-2-(trifluoromethyl)phenyl]-2-methoxy-butyl]1,2,4-triazole; |

Compounds (IC) comprise chiral centers and they are generally obtained in the form of racemates. The R- and S-enantiomers of the compounds can be separated and isolated in pure form with methods known by the skilled person, e.g. by using chiral HPLC. Furthermore, components I can be present in different crystal modifications, which may differ in biological activity. The compounds may be present in various crystal modifications. They are likewise provided by the present invention.

EXAMPLES

The following examples further illustrate the present invention and do not restrict the invention in any manner.

Example 1-1: Synthesis of [4-(4-chlorophenoxy)-2-(trifluoromethyl)phenyl]-cyclopropyl-methanone Steps 1-1a and 1-1b A 500 ml-four-necked flask equipped with a Teflon-blade stirrer, reflux condenser, and a dropping funnel was charged with 94.0 g 2-bromo-5-fluoro-benzotrifluoride (purity 99%, 0.38 mol) and 150 g toluene. A solution of isopropylmagnesium chloride in THF (2M, 243 g, 0.5 mol) was added keeping the temperature between 25 and 30° C. After stirring for 60 min this solution was added to a mixture of 150 g toluene, 61.0 g cyclopropanecarbonyl chloride (0.57 mol), and 1.1 g copper(I)chloride (0.01 mol) in a 1000 ml-four-necked flask equipped with a Teflon-blade stirrer, reflux condenser, and a dropping funnel keeping the temperature between 38 and 42° C. After half of the Grignard solution was dosed another 1.1 g of copper(I)chloride were added. When the Grignard addition was completed the mixture was stirred for 2 h at 40° C. 300 g water were added, the solution was stirred for 10 min and the phases allowed to separate. The organic phase was washed with a mixture of 250 g water and 60 g 25%-ammonia solution. After separation of the phases the organic phase was transferred to a rotary evaporator and the solvent was removed at 40° C. and 10 mbar to leave a dark brown product. This was dissolved in 220 g DMF, and transferred to a 1 l-four-necked flask equipped with a Teflon-blade stirrer, reflux condenser, and a dropping funnel. 68 g potassium carbonate (0.49 mol) and a mixture of 54 g 4-chlorophenol (0.42 mol) and 20 g DMF was added at ambient temperature, the vessel was heated to 130° C. and kept at this temperature for 2 h. The mixture was cooled to 120° C. and the pressure was slowly reduced to 100 mbar. Distillation of the solvent was continued under these conditions until no more condensate was formed. The vessel was cooled to 25° C., 200 ml of toluene followed by 500 g of water were added under stirring. The phases were separated and the aqueous phase was extracted with 200 ml toluene. The combined organic phases were washed with 200 g sodium hydroxide solution (5%) and the lower aqueous phase was separated. The organic phase was transferred to a rotary evaporator and the solvent was removed at 40° C. and 10 mbar to leave 126.4 g of a slightly brown product (purity: 91.5%, 0.34 mol, 88.6% of the theoretical yield).

Example 1-2: Synthesis of [4-(4-chlorophenoxy)-2-(trifluoromethyl)phenyl]-cyclopropyl-methanone Step 1-2a Synthesis of cyclopropyl-[4-fluoro-2-(trifluoromethyl)phenyl]methanone A 500 ml-four-necked flask equipped with a Teflon-blade stirrer, reflux condenser, and a dropping funnel was charged with 94.0 g 2-bromo-5-fluoro-benzotrifluoride (purity 99%, 0.38 mol) and 150 g toluene. A solution of isopropylmagnesium chloride in THF (2M, 243 g, 0.5 mol) was added keeping the temperature between 25 and 30° C. After stirring for 60 min this solution was added to a mixture of 150 g toluene, 61.0 g cyclopropanecarbonyl chloride (0.57 mol), and 1.1 g copper(I)chloride (0.01 mol) in a 1000 ml-four-necked flask equipped with a Teflon-blade stirrer, reflux condenser, and a dropping funnel keeping the temperature between 38 and 42° C. After half of the Grignard solution was dosed another 1.1 g of copper(I)chloride were added. When the Grignard addition was completed the mixture was stirred for 2 h at 40° C. 300 g water were added, the solution was stirred for 10 min and the phases allowed to separate. The organic phase was washed with a mixture of 250 g water and 60 g 25%-ammonia solution. After separation of the phases the organic phase was transferred to a rotary evaporator and the solvent was removed at 40° C. and 10 mbar to leave 89.9 g of a dark brown product (purity: 92.4%, 0.36 mol, 93.4% of the theoretical yield).

Step 1-2b: Synthesis of [4-(4-chlorophenoxy)-2-(trifluoromethyl)phenyl]-cyclopropyl-methanone A 4 l-four-necked flask equipped with a Teflon-blade stirrer, reflux condenser, and a dropping funnel was charged with 91 g [4-fluoro-2-(trifluoromethyl)phenyl]-cyclopropyl-methanone (purity 97%, 0.38 mol), 200 g of DMF, and 68 g potassium carbonate (0.49 mol). A mixture of 54 g 4-chlorophenol (0.42 mol) and 20 g DMF was added at ambient temperature, the vessel was heated to 130° C. and kept at this temperature for 2 h. The vessel was cooled to 25° C., 400 ml of MTBE followed by 750 g of water were added under stirring. The phases were separated and the aqueous phase was extracted with 300 ml MTBE. The combined organic phases were washed with 200 ml sodium hydroxide solution (5%) and the lower aqueous phase was separated. The organic phase was transferred to a rotary evaporator and the solvent was removed at 40° C. and 10 mbar to leave 130.4 g of a slightly brown product (purity: 94.0%, 0.36 mol, 94.6% of the theoretical yield).

Example 2-1: Synthesis of 1-[4-(4-chlorophenoxy)-2-(trifluoromethyl)phenyl]-2-methyl-propan-1-one Steps 2-1a and 2-1b A 2 l-four-necked flask equipped with a Teflon-blade stirrer, reflux condenser, and a dropping funnel was charged with 270.0 g 2-bromo-5-fluoro-benzotrifluoride (purity 99%, 1.1 mol) and 1000 ml toluene. A solution of isopropylmagnesium chloride in THF (2M, 700 g, 1.44 mol) was added keeping the temperature between 25 and 30° C. After stirring for 30 min this solution was added to a mixture of 1000 ml toluene, 167.0 g isobutyric acid chloride (1.57 mol), and 3.5 g copper(I)chloride (0.035 mol) in a 4 l-four-necked flask equipped with a Teflon-blade stirrer, reflux condenser, and a dropping funnel keeping the temperature between 38 and 42° C. After half of the Grignard solution was dosed another 3.5 g of copper(I)chloride were added. When the Grignard addition was completed the mixture was stirred for 1 h at 40° C. 500 g water were added, the solution was stirred for 10 min and the phases allowed to separate. The organic phase was washed with 500 g 10%-ammonia solution. After separation of the phases the organic phase was transferred to a rotary evaporator and the solvent was removed at 40° C. and 10 mbar to leave a brown product. This was dissolved in 700 g DMF, and transferred to a 4 l-four-necked flask equipped with a Teflon-blade stirrer, reflux condenser, and a dropping funnel. 200 g potassium carbonate (1.45 mol) and a mixture of 160 g 4-chlorophenol (0.42 mol) and 60 g DMF was added at ambient temperature, the vessel was heated to 130° C. and kept at this temperature for 1.5 h. The vessel was cooled to 25° C., 1000 ml of MTBE followed by 1000 g of water were added under stirring. The phases were separated and the aqueous phase was extracted with 500 ml MTBE. The combined organic phases were washed with 500 g sodium hydroxide solution (5%) and the lower aqueous phase was separated. The organic phase was transferred to a rotary evaporator and the solvent was removed at 40° C. and 10 mbar to leave 339.4 g of a slightly brown product (purity: 87.3%, 0.86 mol, 78.8% of the theoretical yield).

Example 2-2: Synthesis of 1-[4-(4-chlorophenoxy)-2-(trifluoromethyl)phenyl]-2-methyl-propan-1-one Step 2-2a1: Synthesis of 1-[4-fluoro-2-(trifluoromethyl)phenyl]-2-methyl-propan-1-one A 1 m$^3$-vessel equipped with a 3-level 2-blade stirrer was charged with 100 kg 2-bromo-5-fluoro-benzotrifluoride (purity 99%, 407 mol) and 150 kg of toluene. A solution of isopropylmagnesium chloride in THF (2M, 272 kg, 530 mol) was added keeping the temperature between 25 and 33° C. After stirring for 60 min this solution was transferred to a 1 m$^3$-IBC. The vessel was charged with 150 kg toluene, 65 kg isobutyric acid chloride (611 mol), and 1.2 kg copper(I) chloride (12.2 mol), and the Grignard solution in the IBC was added keeping the temperature between 25 and 40° C. After half of the Grignard solution was dosed another 1.2 kg of copper(I)chloride were added. When the Grignard addition was completed the mixture was stirred for 90 min at 40° C. The vessel was cooled to 10° C. and 200 kg water with a temperature of 5° C. were added, the solution was stirred for 10 min and the phases allowed to separate for 1 h. The lower aqueous phase was separated and the organic phase was washed with a mixture of 100 kg water and 50 kg 25%-ammonia solution. After separation of the phases the organic phase was transferred to an industrial bulk container (IBC). Three identical batches were run, the organic phases of all four batches were combined and the solvents and other volatiles were distilled off at 10 mbar and 40° C. to leave 393 kg of a brown product (purity: 86.7%, 1455 mol, 89.3% of the theoretical yield).

Step 2-2a2: Synthesis of 1-[4-fluoro-2-(trifluoromethyl)phenyl]-2-methyl-propan-1-one A 1000 ml-four-necked flask equipped with a Teflon-blade stirrer, reflux condenser, and a dropping funnel was charged with 200.0 g 2-bromo-5-fluoro-benzotrifluoride (purity 99%, 0.81 mol) and 300 g toluene. A solution of isopropylmagnesium chloride in THF (2M, 544 g, 1.12 mol) was added keeping the temperature between 25 and 30° C. After stirring for 60 min this solution was added to a mixture of 300 g toluene, 165.7 g isobutyric acid chloride (1.59 mol), and 0.243 g copper(I)chloride (0.0025 mol) in a 2000 ml-four-necked flask equipped with a Teflon-blade stirrer, reflux condenser, and a dropping funnel keeping the temperature between 38 and 42° C. After half of the Grignard solution was dosed another 0.243 g of copper(I)chloride were added. When the Grignard addition was completed the mixture was stirred for 2 h at 40° C. 500 g water were added, the solution was stirred for 10 min and the phases allowed to separate. The organic phase was washed with 500 g of a 5%-ammonia solution. After separation of the phases the organic phase was transferred to a rotary evaporator and the solvent was removed at 40° C. and 10 mbar to leave 194.0 g of a dark brown product (purity: 86.2%, 0.71 mol, 87.6% of the theoretical yield).

Step 2-2b1: Synthesis of 1-[4-(4-chlorophenoxy)-2-(trifluoromethyl)phenyl]-2-methyl-propan-1-one A 1 m$^3$-vessel equipped with a 3-level 2-blade stirrer was charged with 100 kg potassium carbonate (723.6 mol) and 128 kg DMF. Technical 1-[4-fluoro-2-(trifluoromethyl)phenyl]-2-methyl-propan-1-one (131 kg, 86.7%, 485 mol) was added at ambient temperature, followed by 132 kg of a solution of 4-chlorophenol in DMF (56.7%, 581.9 mol, 57.16 kg DMF). The feed lines were rinsed with a total of 15 kg DMF. The content of the vessel was heated to 130° C. and kept at this temperature for 3.5 h. The vessel was cooled to 25° C. and a vacuum of 10 mbar was applied. The temperature was raised slowly to 100° C. to distill off most of the DMF and other volatiles. When no more condensate was formed the vessel was flushed with nitrogen and 400 kg of toluene were added followed by 400 kg of water. After 30 min the stirrer was stopped and after additional 60 min the lower aqueous phase was separated. The remaining organic phase was washed with 115 kg sodium hydroxide solution (5%) and the lower aqueous phase was separated. The organic phase was discharged to an IBC to yield 580 kg of a solution containing 27.8% of the desired product (161.2 kg, 470 mol, 97% of the theoretical yield).

Step 2-2b2: Synthesis of 1-[4-(4-chlorophenoxy)-2-(trifluoromethyl)phenyl]-2-methyl-propan-1-one A 100 ml-four-necked flask equipped with a Teflon-blade stirrer, Dean-Stark-trap, and a dropping funnel was charged with 5 g 1-[4-fluoro-2-(trifluoromethyl)phenyl]-2-methyl-propan-1-one (purity 84.7%, 0.0181 mol), 10 g o-xylene, 3.49 g 4-chlorophenol (0.03 mol), and 1.52 g potassium hydroxide solution (50%, 0.03 mol), and was heated to reflux (151° C.) for 5 h. The vessel was cooled to 25° C., 20 ml o-xylene and 20 g water were added under stirring and acidified to pH 4 with 20% hydrochloric acid. The phases were separated and the aqueous phase was twice extracted with 20 ml o-xylene. The combined aqueous phases were extracted with 20 ml o-xylene. The combined organic phases were transferred to a rotary evaporator and the solvent was removed at 40° C. and 10 mbar to leave 7.5 g of a slightly brown product (purity: 78.5%, 0.02 mol, 95.0% of the theoretical yield).

Example 3-1: Synthesis of 4-(4-chlorophenyloxy)-2-trifluoromethyl-acetophenone

Steps 3-1a and 3-1b

A 500 ml-four-necked flask equipped with a Teflon-blade stirrer, reflux condenser, and a dropping funnel was charged with 94.0 g 2-bromo-5-fluoro-benzotrifluoride (purity 99%, 0.38 mol) and 150 g toluene. A solution of isopropylmagnesium chloride in THF (2M, 243 g, 0.5 mol) was added keeping the temperature between 25 and 30° C. After stirring for 30 min this solution was added to a mixture of 150 g toluene, 46.0 g acetyl chloride (0.57 mol), and 1.1 g copper (I)chloride (0.01 mol) in a 1000 ml-four-necked flask equipped with a Teflon-blade stirrer, reflux condenser, and a dropping funnel keeping the temperature between 38 and 42° C. After half of the Grignard solution was dosed another 1.1 g of copper(I)chloride were added. When the Grignard addition was completed the mixture was stirred for 1 h at 40° C. 300 g water were added, the solution was stirred for 10 min and the phases allowed to separate. The organic phase was washed with a mixture of 250 g water and 60 g 25%-ammonia solution. After separation of the phases the organic phase was transferred to a rotary evaporator and the solvent was removed at 40° C. and 10 mbar to leave a brown product. This was dissolved in 220 g DMF, and transferred to a 2 l-four-necked flask equipped with a Teflon-blade stirrer, reflux condenser, and a dropping funnel. 68.0 g potassium carbonate (0.49 mol) and a mixture of 54.0 g 4-chlorophenol (0.42 mol) and 14 g DMF was added at ambient temperature, the vessel was heated to 130° C. and kept at this temperature for 2 h. The vessel was cooled to 25° C., 750 g water followed by 400 ml toluene were added under stirring. The phases were separated. The organic phase was washed with 200 g sodium hydroxide solution (5%) and the lower aqueous phase was separated. The organic phase was transferred to a rotary evaporator and the solvent was removed at 60° C. and 5 mbar to leave 109.7 g of a slightly brown product (purity: 83.8%, 0.29 mol, 76.3% of the theoretical yield).

Example 3-2: Synthesis of 4-(4-chlorophenyloxy)-2-trifluoromethyl-acetophenone

Step 3-2a1: Synthesis of 4-fluoro-2-trifluoromethyl-acetophenone

A 1 l-four-necked flask equipped with a Teflon-blade stirrer, reflux condenser, and a dropping funnel was charged with 96.0 g 2-bromo-5-fluoro-benzotrifluoride (purity 95%, 0.38 mol) and 150 g MTBE. A solution of isopropylmagnesium chloride in THF (2M, 243 g, 0.5 mol) was added keeping the temperature between 25 and 30° C. After stirring for 30 min this solution was added to a mixture of 150 g MTBE, 45.0 g acetyl chloride (0.56 mol), and 1.1 g copper (I)chloride (0.01 mol) in a 2 l-double-walled glass reactor equipped with a 3-level 2-blade stirrer, reflux condenser, and a dropping funnel keeping the temperature between 38 and 42° C. After half of the Grignard solution was dosed another 1.1 g of copper(I)chloride were added. When the Grignard addition was completed the mixture was stirred for 1 h at 40° C. 200 g water were added, the solution was stirred for 10 min and the phases allowed to separate. The organic phase was washed with a mixture of 250 g water and 50 g 25%-ammonia solution. After separation of the phases the organic phase was transferred to a rotary evaporator and the solvent was removed at 40° C. and 10 mbar to leave 78.5 g of a dark brown oil (purity: 95.0%, 0.36 mol, 96.4% of the theoretical yield).

Step 3-2a2: Synthesis of 4-chloro-2-trifluoromethyl-acetophenone

A 500 ml-four-necked flask equipped with a Teflon-blade stirrer, reflux condenser, and a dropping funnel was charged with 94.0 g 2-bromo-5-chloro-benzotrifluoride (purity 96%, 0.35 mol) and 150 g toluene. A solution of isopropylmagnesium chloride in THF (2M, 243 g, 0.5 mol) was added keeping the temperature between 25 and 30° C. After stirring for 60 min this solution was added to a mixture of 150 g toluene, 61.0 g acetyl chloride (0.57 mol), and 0.5 g copper (I)chloride (0.005 mol) in a 1 l-four-necked flask equipped with a Teflon-blade stirrer, reflux condenser, and a dropping funnel keeping the temperature between 38 and 42° C. After half of the Grignard solution was dosed another 0.5 g of copper(I)chloride were added. When the Grignard addition was completed the mixture was stirred for 2.5 h at 40° C. 300 g water were added, the solution was stirred for 10 min and the phases allowed to separate. The organic phase was washed with a mixture of 250 g water and 60 g 25%-ammonia solution. After separation of the phases the organic phase was transferred to a rotary evaporator and the solvent was removed at 40° C. and 10 mbar to leave 94.0 g of a dark brown product (purity: 79.3%, 0.30 mol, 86.2% of the theoretical yield).

Step 3-2a3: Synthesis of 4-fluoro-2-trifluoromethyl-acetophenone

A 2.5 $m^3$-vessel equipped with a 3-level 2-blade stirrer was charged with 250 kg 2-bromo-5-fluoro-benzotrifluoride (purity 99%, 1019 mol) and 375 kg toluene. A solution of isopropylmagnesium chloride in THF (2M, 681 kg, 1397 mol) was added keeping the temperature between 25 and 33° C. After stirring for 45 min this solution was transferred to 1 $m^3$-IBCs. The vessel was charged with 375 kg toluene, 120 kg acetyl chloride (1498 mol), and 3.0 kg copper(I)chloride (30.3 mol), and the Grignard solution in the IBCs was added keeping the temperature between 25 and 40° C. After half of the Grignard solution was dosed another 3.0 kg of copper (I)chloride were added. When the Grignard addition was completed the mixture was stirred for 90 min at 40° C. The vessel was cooled to 10° C. and 500 kg water precooled to 10° C. were added, the solution was stirred for 10 min and the phases allowed to separate for 1 h. The lower aqueous phase was separated and the organic phase was washed with a mixture of 250 kg water and 25 kg 25%-ammonia solution. After separation of the phases the organic phase was transferred to IBCs and gave 1677 kg of a slightly brown solution containing 10.4% of the desired product (846 mol, 82.8% of the theoretical yield).

Step 3-2a4: Synthesis of 4-fluoro-2-trifluoromethyl-acetophenone

A 500 ml-four-necked flask equipped with a Teflon-blade stirrer, reflux condenser, and a dropping funnel was charged with 94.0 g 2-bromo-5-fluoro-benzotrifluoride (purity 99%, 0.38 mol) and 150 g toluene. A solution of isopropylmagnesium chloride in THF (2M, 243 g, 0.5 mol) was added keeping the temperature between 25 and 30° C. After stirring for 30 min this solution was added to a mixture of 150 g toluene, 46.0 g acetyl chloride (0.57 mol), and 0.76 g copper(I)chloride (0.0077 mol) in a 1000 ml-four-necked flask equipped with a Teflon-blade stirrer, reflux condenser, and a dropping funnel keeping the temperature between 38 and 42° C. 300 g water were added, the mixture was stirred for 10 min and the phases allowed to separate. The organic phase was washed with 300 g water. After separation of the phases the organic phase was transferred to a rotary evaporator and the solvent was removed at 40° C. and 10 mbar to leave 81.4 g of a brown oil (purity: 81.6%, 0.32 mol, 184.1% of the theoretical yield). The condensate contained 3.9 g of the product (additional 5.0% yield).

Step 3-2a5: Synthesis of 4-fluoro-2-trifluoromethyl-acetophenone

A 1 l-four-necked flask equipped with a Teflon-blade stirrer, reflux condenser, and a dropping funnel was charged with 94.0 g 2-bromo-5-fluoro-benzotrifluoride (purity 99%, 0.38 mol) and 150 g toluene. A solution of isopropylmagnesium chloride in THF (2M, 243 g, 0.5 mol) was added keeping the temperature between 25 and 30° C. After stirring for 30 min this solution was added to a mixture of 150 g toluene, 6.0 g acetyl chloride (0.076 mol), and 0.76 g copper(I)chloride (0.0077 mol) in a 1000 ml-four-necked flask equipped with a Teflon-blade stirrer, reflux condenser, and a dropping funnel keeping the temperature between 38 and 42° C. Parallel to this dosing 40 g acetyl chloride (0.51 mol) were added. When the addition was completed the mixture was stirred for 1 h at 40° C. 300 g water were added, the solution was stirred for 10 min and the phases allowed to separate. The organic phase was washed with 300 g water. After separation of the phases the organic phase was transferred to a rotary evaporator and the solvent was removed at 40° C. and 10 mbar to leave 81.8 g of a brown oil (purity: 80.5%, 0.32 mol, 83.4% of the theoretical yield). The condensate contained 3.3 g of the product (4.2% yield).

Step 3-2b1: Synthesis of 4-(4-chlorophenyloxy)-2-trifluoromethyl-acetophenone

A 2.5 m$^3$-vessel equipped with a 3-level 2-blade stirrer was charged with 250 kg potassium carbonate (1809 mol) and 460 kg DMF. Technical 4-fluoro-2-trifluoromethyl-acetophenone (260 kg, 77.7%, 979 mol) was added at ambient temperature, followed by 310 kg of a solution of 4-chlorophenol in DMF (57%, 1375 mol, 133.3 kg DMF). The feed lines were rinsed with a total of 25 kg DMF. The content of the vessel was heated to 130° C. and kept at this temperature for 3.5 h. The vessel was cooled to 25° C. and a vacuum of 10 mbar was applied. The temperature was raised slowly to 100° C. to distill off most of the DMF and other volatiles. When no more condensate was formed the vessel was flushed with nitrogen and 1000 kg of toluene were added followed by 1000 kg of water. After 30 min the stirrer was stopped and after additional 60 min the lower aqueous phase was separated. The remaining organic phase was washed with 350 kg sodium hydroxide solution (5%) and the lower aqueous phase was separated. The organic phase was discharged to IBCs to yield 1381 kg of a solution containing 22.0% of the desired product (304.2 kg, 967 mol, 98.7% of the theoretical yield).

Step 3-2b2: Synthesis of 4-(4-chlorophenyloxy)-2-trifluoromethyl-acetophenone

A 500 ml-four-necked flask equipped with a Teflon-blade stirrer, Dean-Stark-trap, and a dropping funnel was charged with 100 g 4-fluoro-2-trifluoromethyl-acetophenone (purity 78%, 0.38 mol), 100 g o-xylene, 54 g 4-chlorophenol (0.42 mol), and 78.5 g potassium carbonate (0.57 mol). The vessel was heated to reflux for 5 h removing 4.8 g of water. The vessel was cooled to 25° C., 250 ml o-xylene and 320 g of water were added under stirring. The phases were separated and the aqueous phase was extracted with 100 ml o-xylene. The combined organic phases were washed with 100 g sodium hydroxide solution (10%) and the lower aqueous phase was separated. The organic phase was transferred to a rotary evaporator and the solvent was removed at 40° C. and 10 mbar to leave 137.2 g of a slightly brown product (purity: 82.6%, 0.36 mol, 95.2% of the theoretical yield).

Step 3-2b3: Synthesis of 4-(4-chlorophenyloxy)-2-trifluoromethyl-acetophenone

A 100 ml pressure vessel (Premex) equipped with a mechanical stirrer was charged with 20 g 4-fluoro-2-trifluoromethyl-acetophenone (purity 78%, 0.08 mol), 20 g toluene, 13.6 g 4-chlorophenol (0.11 mol), and 6.4 g potassium hydroxide (0.11 mol). The vessel was sealed and heated to 153° C. for 5 h. After cooling and depressurizing the reaction mixture was transferred to a separating funnel containing 20 g toluene and 40 g water and acidified to pH 4 with 20% hydrochloric acid. The aqueous phase was separated and the organic phase was transferred to a rotary evaporator and the solvent was removed at 40° C. and 10 mbar to leave 28.5 g of a slightly brown product (purity: 73.3%, 0.07 mol, 87.7% of the theoretical yield).

Step 3-2b4: Synthesis of 4-(4-chlorophenyloxy)-2-trifluoromethyl-acetophenone

A 100 ml-four-necked flask equipped with a Teflon-blade stirrer, reflux condenser, and a dropping funnel was charged with 5.7 g 4-chloro-2-trifluoromethyl-acetophenone (purity 81.0%, 20.7 mmol), 10 g N-methyl pyrrolidone, 3.2 g 4-chlorophenol (24.9 mmol), and 3.3 g sodium carbonate (31.1 mmol), and was heated 180° C. for 17 h. The vessel was cooled to 25° C. and the solvent was removed at a rotary evaporator at 60° C./8 mbar. 50 ml toluene and 40 g water were added under stirring, the phases were separated and the organic phase was washed with 10 g water. The combined aqueous phases were extracted with 10 ml toluene. The combined organic phases were transferred to a rotary evaporator and the solvent was removed at 40° C. and 10 mbar to leave 8.1 g of a slightly brown product (purity: 66.7%, 17.2 mmol, 82.8% of the theoretical yield).

Step 3-2b5: Synthesis of 4-(4-chlorophenyloxy)-2-trifluoromethyl-acetophenone

A 500 ml-four-necked flask equipped with a Teflon-blade stirrer, reflux condenser, and a dropping funnel was charged with 9.0 g 4-chloro-2-trifluoromethyl-acetophenone (purity 78.8%, 31.9 mmol), 15 g Dimethyl imidazolidinone, 5.3 g 4-chlorophenol (41.2 mmol), and 7.4 g potassium carbonate (53.5 mmol), and was heated 170° C. for 6 h. The vessel was cooled to 25° C. and 40 ml toluene and 35 g water were added under stirring, the phases were separated and the organic phase was washed with 20 g 5% sodium hydroxide solution. The phases were separated, the organic phase was transferred to a rotary evaporator and the solvent was removed at 40° C. and 10 mbar to leave 16.0 g of a brownish product (purity: 50.2%, 25.5 mmol, 80.1% of the theoretical yield).

Step 3-2b6: Synthesis of 4-(4-chlorophenyloxy)-2-trifluoromethyl-acetophenone A 20 ml microwave vial equipped with a magnetic stirring bar was charged with 6.0 g 4-fluoro-2-trifluoromethyl-acetophenone (purity 78.0%, 22.7 mmol), and 4.8 g sodium 4-chloro phenolate (31.8 mmol), and was heated in a microwave oven to 160° C. for 3 h. The vessel was cooled to 25° C., and rinsed with 30 ml toluene and 20 g 10% hydrochloric acid into a separating funnel. The phases were separated, the aqueous phase was extracted with 6 ml toluene, the combined organic phases were transferred to a rotary evaporator and the solvent was removed at 40° C. and 10 mbar to leave 8.7 g of a brownish product (purity: 75.52%, 20.9 mmol, 91.9% of the theoretical yield).

Step 3-2b7: Synthesis of 4-(4-chlorophenyloxy)-2-trifluoromethyl-acetophenone A 20 ml microwave vial equipped with a magnetic stirring bar was charged with 6.0 g 4-fluoro-2-trifluoromethyl-acetophenone (purity 78.0%, 22.7 mmol), 6 g toluene, and 5.3 g potassium 4-chloro phenolate (31.8 mmol), and was heated in a microwave oven to 160° C. for 3 h. The vessel was cooled to 25° C., and rinsed with 20 g toluene and 20 g 10% hydrochloric acid into a separating funnel. The phases were separated, the aqueous phase was extracted with 5 ml toluene, the combined organic phases were transferred to a rotary evaporator and the solvent was removed at 40° C. and 10 mbar to leave 9.3 g of a brownish product (purity: 74.0%, 21.9 mmol, 96.3% of the theoretical yield).

Example 4

Preparation of 2-Acyl-5-halogeno-benzotrifluorides Using Mg

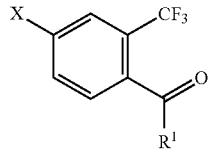

Example 4a

4-fluoro-2-(trifluoromethyl)-acetophenone

A 500 ml-four-necked flask equipped with a Teflon-blade stirrer, reflux condenser, and a dropping funnel was charged with 1.10 g magnesium metal chips (45 mmol) and 50 g THF. 1 g of a 2M solution of isopropyl magnesium chloride was added for activation. 10 g 2-bromo-5-fluoro-benzotrifluoride (purity 99%, 41 mmol) were added within 60 min, the temperature rose to 52° C. After stirring for 60 min this Grignard solution was decanted from the remaining metal, transferred to a dropping funnel, and added within 60 min to a mixture of 50 g toluene, 4.8 g acetyl chloride (61 mmol), and 0.08 g copper(I)chloride (0.8 mmol) in a 500 ml-four-necked flask equipped with a Teflon-blade stirrer, reflux condenser, and a dropping funnel keeping the temperature between 38 and 42° C. When the Grignard addition was completed the mixture was stirred for 1 h at 40° C. 50 g water were added, the solution was stirred for 10 min and the phases allowed to separate. The organic phase was washed with 25 g water. After separation of the phases the organic phase was transferred to a rotary evaporator and the solvent was removed at 40° C. and 10 mbar to leave 9.2 g of a dark brown product (purity: 59.5%, 27 mmol, 65% of the theoretical yield).

Example 4b

4-fluoro-2-(trifluoromethyl)-acetophenone

A 500 ml-four-necked flask equipped with a Teflon-blade stirrer, reflux condenser, and a dropping funnel was charged with 0.90 g magnesium metal chips (37 mmol) and 40 g THF. 1 g of a 2M solution of isopropyl magnesium chloride was added for activation. 10 g 2-bromo-5-fluoro-benzotrifluoride (purity 99%, 41 mmol) were added within 60 min, the temperature rose to 50° C. After stirring for 60 min all magnesium had vanished and the Grignard solution was transferred to a dropping funnel, and added within 60 min to a mixture of 40 g toluene, 4.0 g acetyl chloride (51 mmol), and 0.08 g copper(I)chloride (0.8 mmol) in a 500 ml-four-necked flask equipped with a Teflon-blade stirrer, reflux condenser, and a dropping funnel keeping the temperature between 38 and 42° C. When the Grignard addition was completed the mixture was stirred for 1 h at 40° C. 30 g water were added, the solution was stirred for 10 min and the phases allowed to separate. The organic phase was washed with 25 g water. After separation of the phases the organic phase was transferred to a rotary evaporator and the solvent was removed at 40° C. and 10 mbar to leave 9.2 g of a dark brown product (purity: 60.9%, 27 mmol, 74% of the theoretical yield based on Mg).

The invention claimed is:

1. A process for the preparation of the ketone compounds (IA)

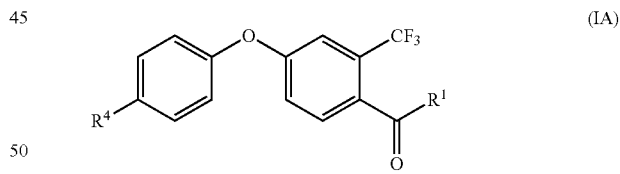

comprising the following steps:

reacting a compound of the formula (III)

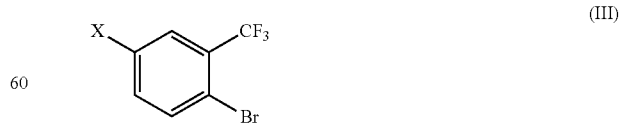

with $R^1$—Mg-Hal (IV) or Mg and $R^1C(=O)Cl$ (V) in the presence of a Cu(I)-catalyst in an amount of 0.005 to 0.065 mole equivalents per 1 mole of compound (III), to result in compounds II

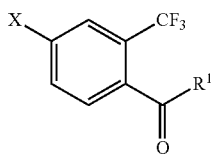

(II)

wherein the compound of the formula (III) is reacted with R'—Mg-Hal (IV) in the absence of or essentially without AlCl$_3$;

and (ii) reacting compound (II) as defined in step (i) with a phenol derivative of formula (VI)

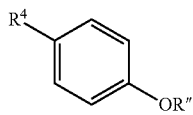

(VI)

in the presence of a base if R" is hydrogen;
wherein the variables are defined as follows:
X is F or Cl;
R$^1$ is C$_1$-C$_6$-alkyl or C$_3$-C$_8$-cycloalkyl; and
R$^4$ is F or Cl;
R' is C$_1$-C$_4$-alkyl or C$_3$-C$_6$-cycloalkyl;
Hal is halogen; and
R" is hydrogen or an alkali metal cation.

2. The process of claim 1, wherein the Cu(I)-catalyst is Cu(I)Cl.

3. The process of claim 1, wherein R' is iso-propyl.

4. The process of claim 1, wherein Hal is Br or Cl.

5. The process of claim 1, wherein X is F.

6. The process of claim 1, wherein R$^1$ is selected from CH$_3$, CH(CH$_3$)$_2$ and cyclopropyl.

7. The process of claim 1, wherein R$^4$ is Cl.

8. The process of claim 1, wherein during process step (i) the Grignard compound(s) Ga and/or Gb

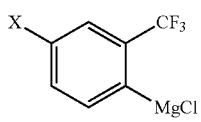

(Ga)

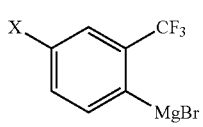

(Ga)

is/are formed, wherein X is F or Cl.

9. A process for the preparation of triazole compounds of the formula (IC)

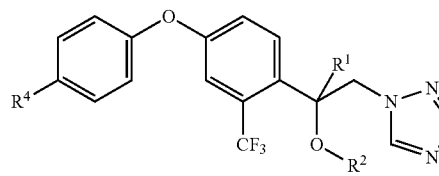

(IC)

wherein

R$^1$ is C$_1$-C$_6$-alkyl or C$_3$-C$_8$-cycloalkyl;

R$^2$ is hydrogen, C$_1$-C$_6$-alkyl, C$_2$-C$_6$-alkenyl, C$_2$-C$_6$-alkynyl, C$_3$-C$_8$-cycloalkyl, C$_3$-C$_8$-cycloalkyl-C$_1$-C$_6$-alkyl, phenyl, phenyl-C$_1$-C$_4$-alkyl, phenyl-C$_2$-C$_4$-alkenyl or phenyl-C$_2$-C$_4$-alkynyl;

wherein the aliphatic moieties of R$^2$ are not further substituted or do carry one, two, three or up to the maximum possible number of identical or different groups R$^{12a}$ which independently are selected from:

halogen, OH, CN, nitro, C$_1$-C$_4$-alkoxy, C$_3$-C$_8$-cycloalkyl, C$_3$-C$_8$-halocycloalkyl and C$_1$-C$_4$-halogenalkoxy;

wherein the cycloalkyl and/or phenyl moieties of R$^2$ are not further substituted or do carry one, two, three, four, five or up to the maximum number of identical or different groups R$^{12b}$ which independently are selected from:

R$^{12b}$ halogen, OH, CN, nitro, C$_1$-C$_4$-alkyl, C$_1$-C$_4$-alkoxy, C$_1$-C$_4$-halogenalkyl, C$_3$-C$_8$-cycloalkyl, C$_3$-C$_8$-halocycloalkyl and C$_1$-C$_4$-halogenalkoxy; and R$^4$ is F or Cl;

comprising the following steps:

(i) reacting a compound of the formula (III)

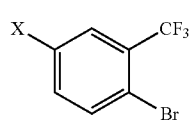

(III)

with R'—Mg-Hal (IV) or Mg and R$^1$C(=O)C$_1$ (V) in the presence of a Cu(I)-catalyst in an amount of 0.005 to 0.065 mole equivalents per 1 mole of compound (III), to result in compounds II

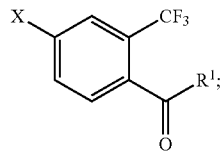

(II)

wherein the compound of the formula (III) is reacted with R'OMgOHal (IV) in the absence of or essentially without AlCl3;

(ii) reacting compound (II) as defined in step (i) with a phenol derivative of formula (VI)

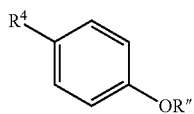

in the presence of a base if R" is hydrogen;
wherein the variables are defined as follows:
X is F or Cl;
$R^1$ is $C_1$-$C_6$-alkyl or $C_3$-$C_8$-cycloalkyl; and
$R^4$ is F or Cl;
R' is $C_1$-$C_4$-alkyl or $C_3$-$C_6$-cycloalkyl;
Hal is halogen; and
R" is hydrogen or an alkali metal cation;
to result in compounds of the formula (IA)

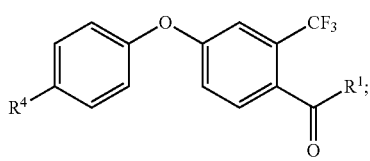

(iii) reacting a ketone of the formula (IA) as defined in step (ii) to oxiranes (IB);

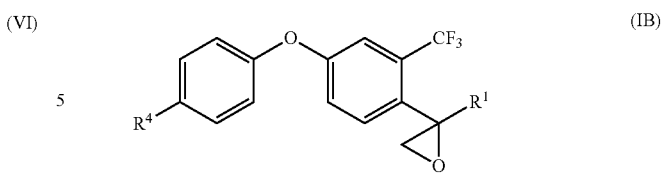

and (iv) reacting the oxirane (IB) as defined in step (iii) with 1H-1,2,4-triazole in the presence of a base to obtain compounds (IC), wherein $R^2$ is hydrogen (compounds IC-1);

and, for obtaining compounds wherein $R^2$ is different from hydrogen:

(v) derivatizing the compound of formula (IC-1) as defined in step (iv) under basic conditions with $R^2$-LG, wherein LG is a nucleophilically replaceable leaving group; to result in compounds (IC-2).

10. The process of claim 9, wherein the reaction to the oxirane (IB) is carried out with a trimethylsulf(ox)onium halide $((CH_3)_3S^+ (O)Hal^-)$ (VII), wherein Hal is halogen, or trimethylsulfonium methylsulfate of the formula (VIII) $(CH_3)_3S^+ CH_3SO_4^-$.

* * * * *